US009010031B1

(12) United States Patent
Webb et al.

(10) Patent No.: US 9,010,031 B1
(45) Date of Patent: Apr. 21, 2015

(54) MODULAR MEDICAL HEADWALL SYSTEM

(71) Applicant: Modular Services Company, Oklahoma City, OK (US)

(72) Inventors: Travis W. Webb, Tuttle, OK (US); Taylor C. Culpepper, Oklahoma City, OK (US); John R. Pierson, Guthrie, OK (US)

(73) Assignee: Modular Services Company, Oklahoma City, OK (US)

( * ) Notice: Subject to any disclaimer, the term of this patent is extended or adjusted under 35 U.S.C. 154(b) by 0 days.

(21) Appl. No.: 14/015,672

(22) Filed: Aug. 30, 2013

Related U.S. Application Data

(60) Provisional application No. 61/867,828, filed on Aug. 20, 2013.

(51) Int. Cl.
*E04H 1/00* (2006.01)
*A61G 12/00* (2006.01)

(52) U.S. Cl.
CPC ...................................... *A61G 12/00* (2013.01)

(58) Field of Classification Search
CPC ....... E04B 2/76; E04B 2/7457; E04B 2/7453; E04B 2/7407
USPC .................. 52/27, 238.1, 239, 241, 242, 243, 52/243.1, 36.1, 36.2, 36.4, 36.5, 36.6, 52/220.1, 220.5, 220.7, 126.1, 126.2, 52/126.3, 127.5, 127.6, 127.7, 656.1, 52/481.1, 481.2, 489.1, 489.2; 174/481, 174/503, 50; 220/477; 160/135, 351, 40
See application file for complete search history.

(56) References Cited

U.S. PATENT DOCUMENTS 3,421,459 A * 1/1969 Sherwood ........................ 108/13
4,905,428 A * 3/1990 Sykes ........................... 52/126.4
(Continued)

FOREIGN PATENT DOCUMENTS

| CA | 2392270 A1 | 8/2007 |
| CA | 2467300 A1 | 7/2011 |
| MX | 262578 | 11/2008 |

OTHER PUBLICATIONS

Carina Picture Frame Inc., "30 Inch Hangm Products Z-bar Hanger Mirror Hanging How to Hang," [online]webpage retrieved from http://123frame.net/30haprzhamih.html, Irvine, Ca. The first publication date of this reference is unknown. This document was published prior to the effective filing date, namely, Aug. 30, 2013, and prior to any foreign priority date of the present application.[retrieved on Jun. 20, 2014].

(Continued)

*Primary Examiner* — Beth Stephan
(74) *Attorney, Agent, or Firm* — Mary M. Lee

(57) ABSTRACT

A modular headwall system with multiple interlocking sections. The studs in each frame section include hooks and slots that ensure secure attachment of one section to each adjacent section while maintaining proper alignment. For floor-mounted applications, a self-leveling base assembly provides a level support track even on uneven floors. An adjustable crown molding assembly provides an attractive architectural feature while concealing an irregular ceiling line. The cover panels forming the front of the headwall float on a hanger system that allows slight lateral and vertical movement while holding the entire matrix of panels firmly against the frame behind it; this allows the panels to maintain proper alignment in the assembled headwall even where the supporting wall and floor surfaces are irregular. The side trim assembly includes a cable management recess. Some panels include a floating equipment track that is aesthetically pleasing and less likely to harbor microorganisms.

17 Claims, 45 Drawing Sheets

(56) References Cited

U.S. PATENT DOCUMENTS

| | | | |
|---|---|---|---|
| 5,097,643 A * | 3/1992 | Wittler | 52/238.1 |
| 5,247,962 A | 9/1993 | Walker | |
| 5,377,467 A * | 1/1995 | Barnavol | 52/238.1 |
| 5,448,859 A | 9/1995 | Walker et al. | |
| 5,644,876 A | 7/1997 | Walker | |
| 5,778,612 A * | 7/1998 | Kissinger et al. | 52/205 |
| 5,906,080 A * | 5/1999 | diGirolamo et al. | 52/243.1 |
| 6,023,896 A * | 2/2000 | Rothschild | 52/243.1 |
| 6,088,980 A * | 7/2000 | Gulliver | 52/239 |
| D443,365 S | 6/2001 | Walker | |
| 6,256,935 B1 | 7/2001 | Walker | |
| 6,269,594 B1 | 8/2001 | Walker | |
| D452,573 S | 12/2001 | Walker | |
| 6,389,773 B1 * | 5/2002 | Reuter et al. | 52/582.2 |
| D472,325 S | 3/2003 | Walker | |
| 6,557,310 B2 * | 5/2003 | Marshall et al. | 52/220.1 |
| 6,668,493 B1 | 12/2003 | Walker | |
| 6,688,056 B2 * | 2/2004 | Von Hoyningen Huene et al. | 52/243.1 |
| 6,711,871 B2 * | 3/2004 | Beirise et al. | 52/782.1 |
| 6,805,185 B2 * | 10/2004 | Gravel et al. | 160/135 |
| 6,854,233 B2 * | 2/2005 | Pitsch et al. | 52/584.1 |
| 6,964,138 B2 * | 11/2005 | Carroll et al. | 52/239 |
| 7,204,714 B2 | 4/2007 | Walker et al. | |
| 7,310,918 B1 * | 12/2007 | Reuter et al. | 52/220.7 |
| 7,461,484 B2 * | 12/2008 | Battey et al. | 52/220.7 |
| 7,549,893 B1 | 6/2009 | Walker et al. | |
| 7,595,446 B2 * | 9/2009 | Turcovsky et al. | 174/50 |
| 7,679,007 B1 | 3/2010 | Walker et al. | |
| 7,770,860 B1 | 8/2010 | Culpepper et al. | |
| 7,775,000 B2 | 8/2010 | Walker et al. | |
| 7,845,601 B1 | 12/2010 | Culpepper et al. | |
| 7,950,189 B1 | 5/2011 | Walker et al. | |
| 7,971,396 B1 | 7/2011 | Culpepper | |
| 8,061,099 B2 * | 11/2011 | Andrews | 52/483.1 |
| 8,186,108 B1 | 5/2012 | Culpepper | |
| 2002/0104271 A1 * | 8/2002 | Gallant | 52/36.1 |
| 2003/0041540 A1 * | 3/2003 | Gravel et al. | 52/239 |
| 2003/0177713 A1 | 9/2003 | Walker et al. | |
| 2004/0231248 A1 | 11/2004 | Walker et al. | |
| 2004/0250480 A1 * | 12/2004 | Matthai | 52/36.1 |
| 2008/0053016 A1 * | 3/2008 | Kang et al. | 52/243.1 |
| 2009/0084055 A1 * | 4/2009 | Mangiardi et al. | 52/357 |
| 2009/0313928 A1 * | 12/2009 | Montgomery | 52/309.1 |
| 2012/0151861 A1 * | 6/2012 | Mulhair | 52/506.05 |

OTHER PUBLICATIONS

Hangman Products "Canvas Hanger," [online] webpage retrieved from http://www.hangmanproducts.com/collections/hanging-solutions/products/canvas-hanger, Woodland Hills, Ca. The first publication date of this reference is unknown. This document was published prior to the effective filing date, namely, Aug. 30, 2013, and prior to any foreign priority date of the present application. [retrieved on Jun. 20, 2014].

Hooks and Lattice, "Cleat Hangers, . . . ," [online] webpage retrieved from http://www.hooksandlattice.com/cleat-hangers.html, Jacksonville, Fl. The first publication date of this reference is unknown. This document was published prior to the effective filing date, namely, Aug. 30, 2013, and prior to any foreign priority date of the present application. [retrieved on Sep. 25, 2012].

Signaturecomponents.com, "Flush Mount Interlocking Mounting Bracket," [online] webpage retrieved from http://www.signaturecomponents.com/flush-mount-interlocking-bracket-p/sc-k4. The first publication date of this reference is unknown. This document was published prior to the effective filing date, namely, Aug. 30, 2013, and prior to any foreign priority date of the present application. [retrieved on Sep. 25, 2012].

Hangman Products, "Hangman Product Hangnail," [online] webpage retrieved from http://www.hangmanstore.com/hangman-products-heavy-duty-hangnail-system-p/hn.htm, Woodland Hills, Ca. The first publication date of this reference is unknown. This document was published prior to the effective filing date, namely, Aug. 30, 2013, and prior to any foreign priority date of the present application. [retrieved on Sep. 25, 2012].

Picture Hang Solutions, "Cleat Picture Hangers," [online] webpage retrieved from http://www.govart.com/hardware_cleat.html, Chapel Hill, N.C. The first publication date of this reference is unknown. This document was published prior to the effective filing date, namely, Aug. 30, 2013, and prior to any foreign priority date of the present application. [retrieved on Sep. 25, 2012].

Rockler Companies, Inc, "Extra Thin Flush Mount," [online] webpage retrieved from http://www.rockler.com/product.cfm?page=344, Medina, MN. The first publication date of this reference is unknown. This document was published prior to the effective filing date, namely, Aug. 30, 2013, and prior to any foreign priority date of the present application. [retrieved on Sep. 25, 2012].

Hangman Products, "Channel Locks Over Edge," [online] webpage retrieved from http://a248,.e.akamai.net/origin-cdn.volusion.com/xt3cs.mx94/v/vspfiles/photos/alh-2jpg,Woodland Hills, Ca. The first publication date of this reference is unknown. This document was published prior to the effective filing date, namely, Aug. 30, 2013, and prior to any foreign priority date of the present application. [retrieved Sep. 25, 2012].

Rockler Companies Inc, "Steel Cleats," [online] webpage retrieved from http://www.rockler.com/product.cfm?page=347, Medina, MN. The first publication date of this reference is unknown. This document was published prior to the effective filing date, namely, Aug. 30, 2013, and prior to any foreign priority date of the present application. [retrieved on Sep. 25, 2012].

* cited by examiner

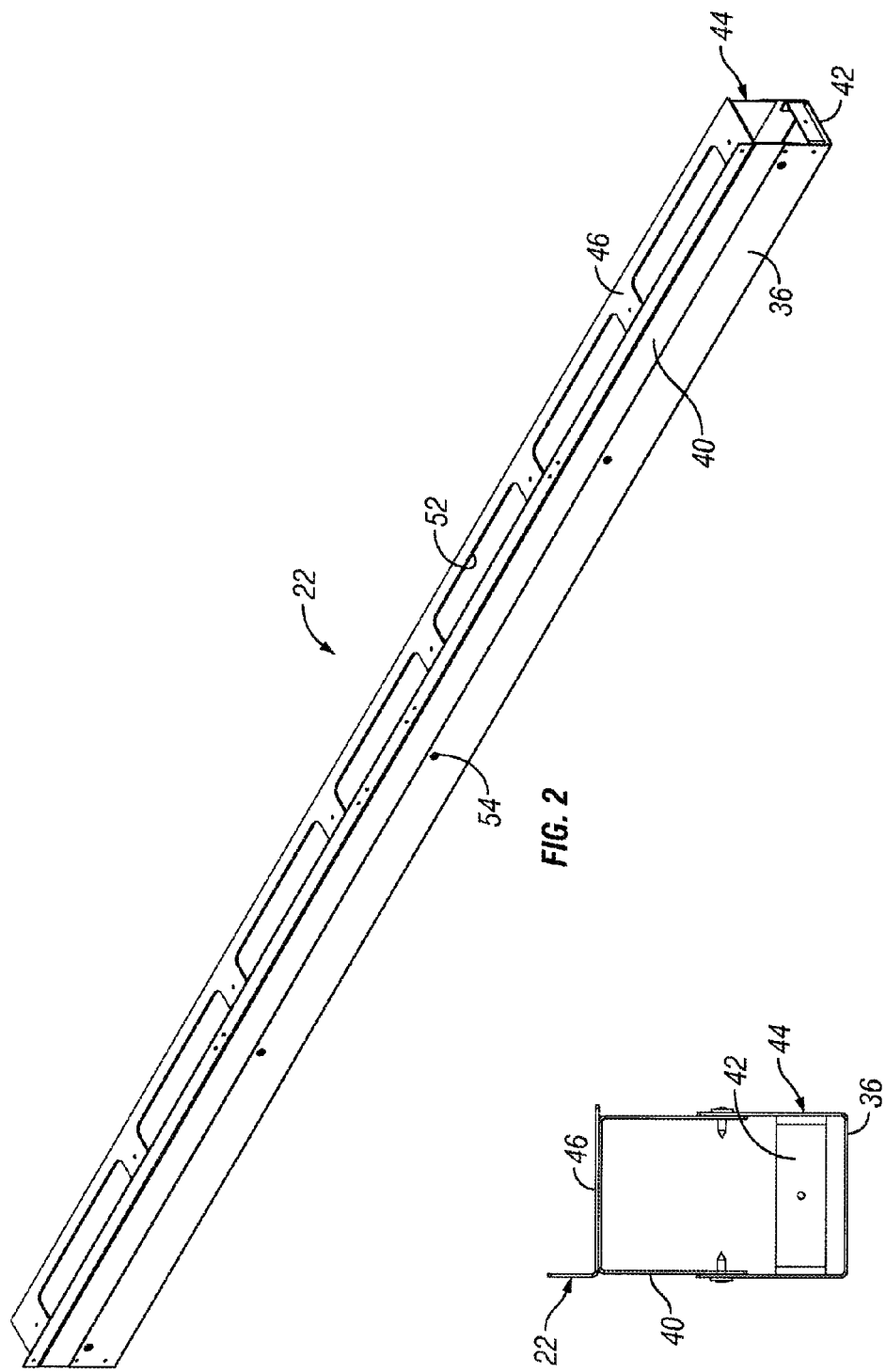

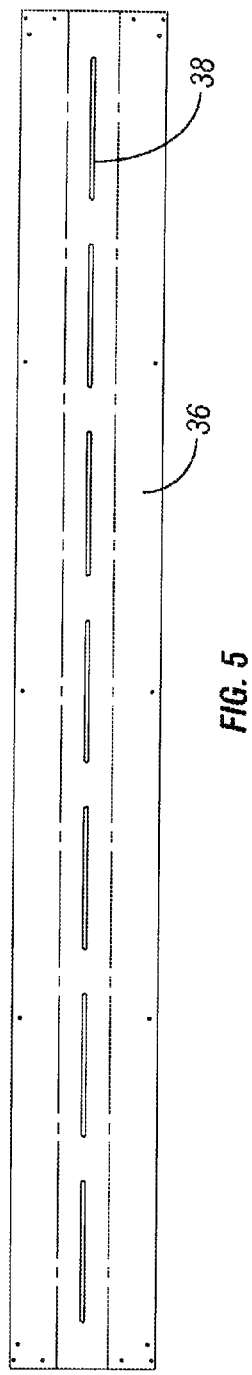
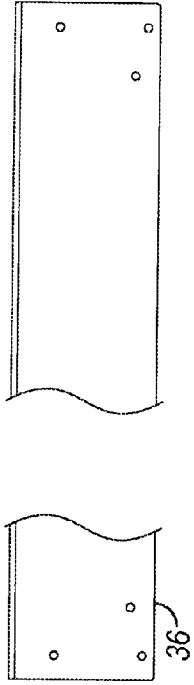
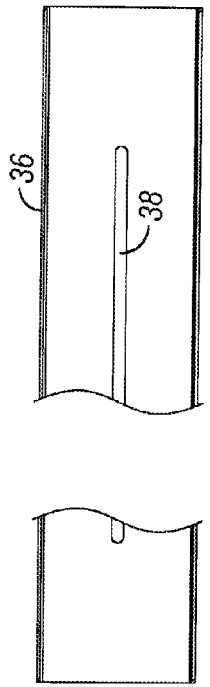
FIG. 5
FIG. 7
FIG. 8
FIG. 6

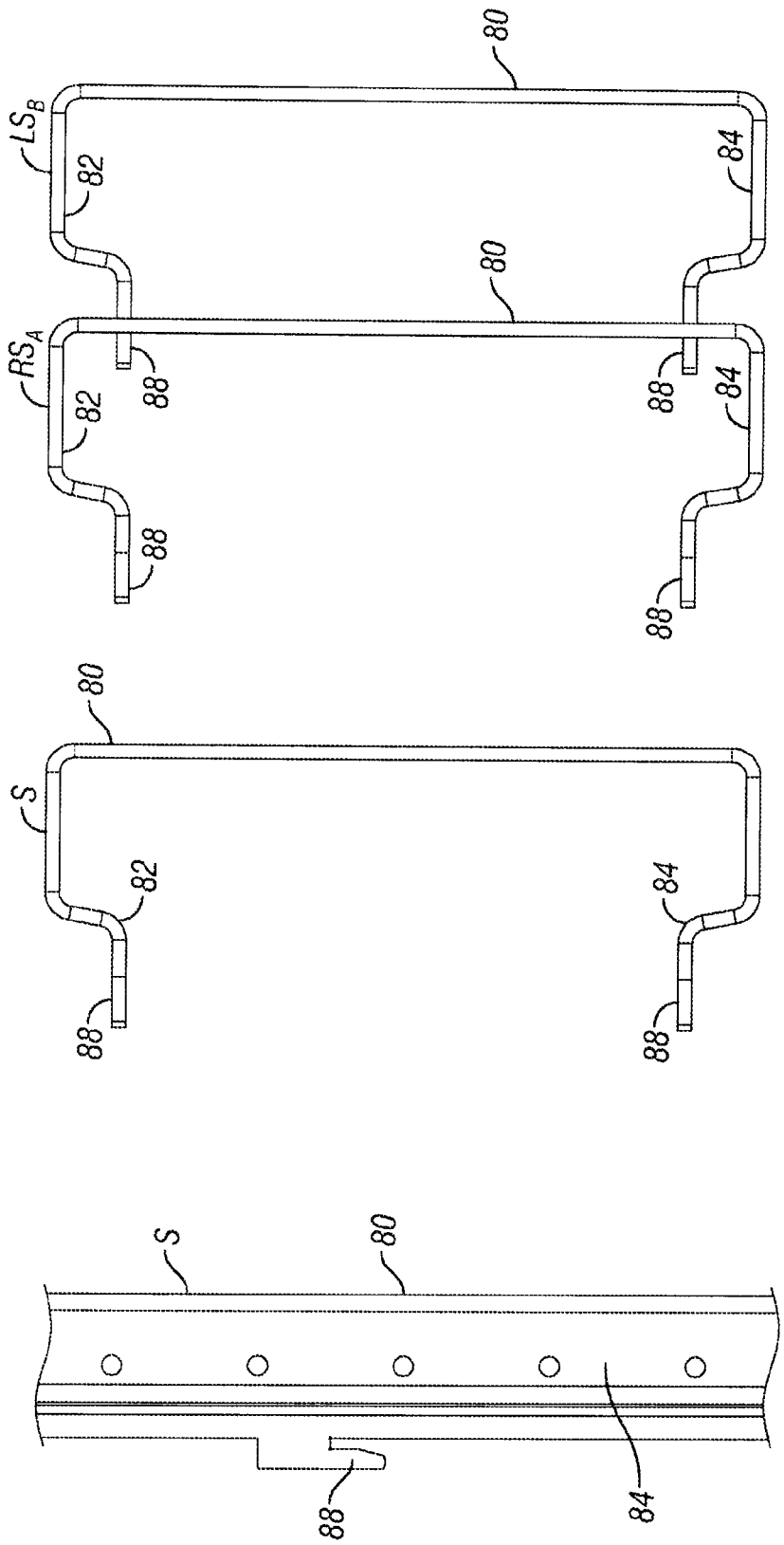

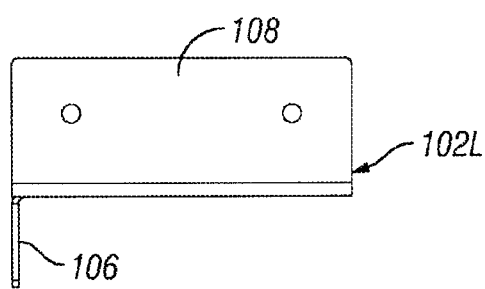
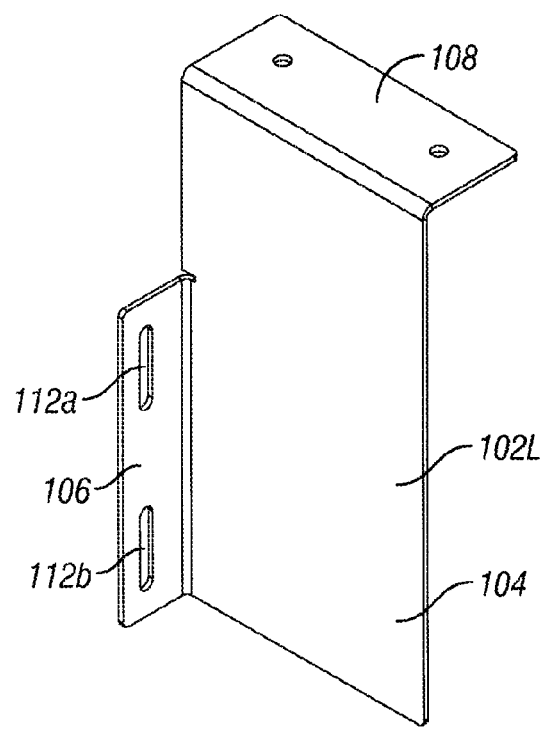
FIG. 49  FIG. 50
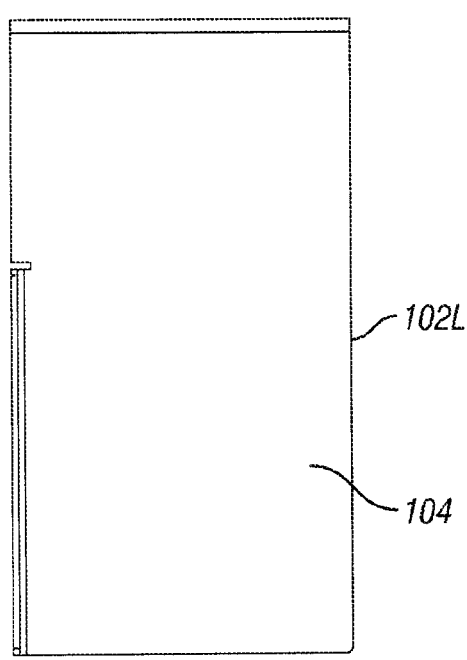
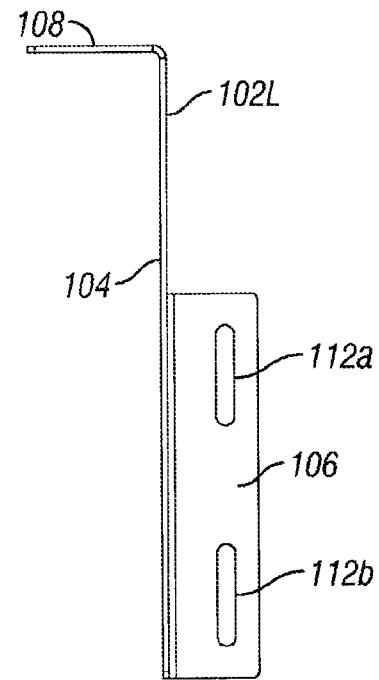
FIG. 51  FIG. 52

FIG. 60
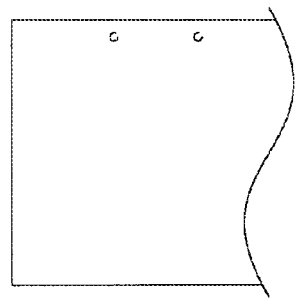 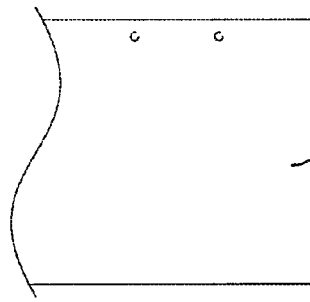 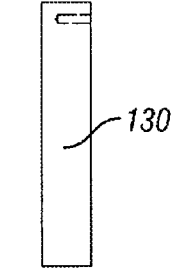
FIG. 61 FIG. 62
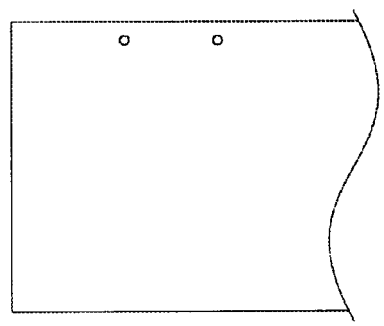 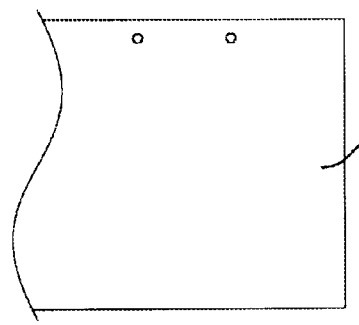
FIG. 63

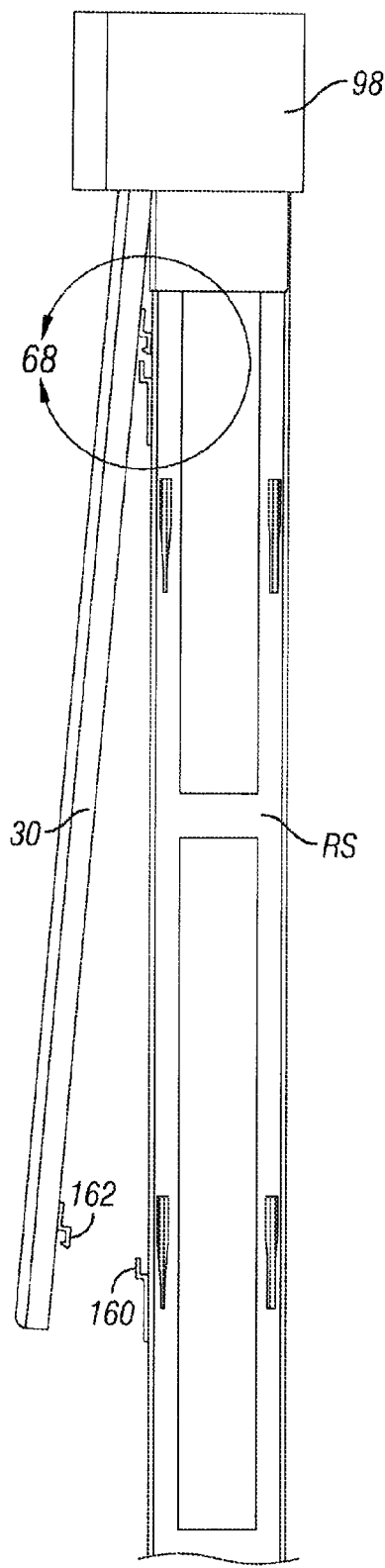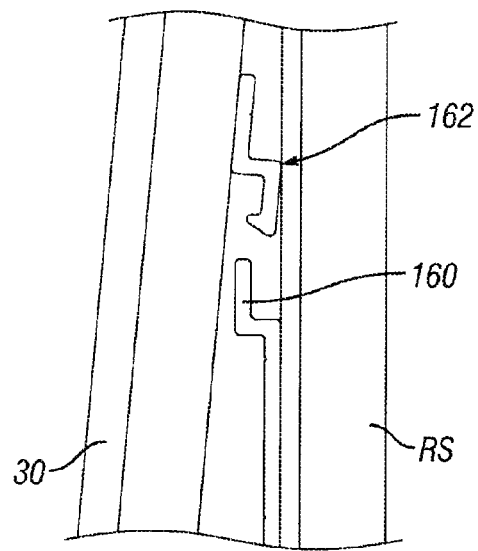
FIG. 68
FIG. 67

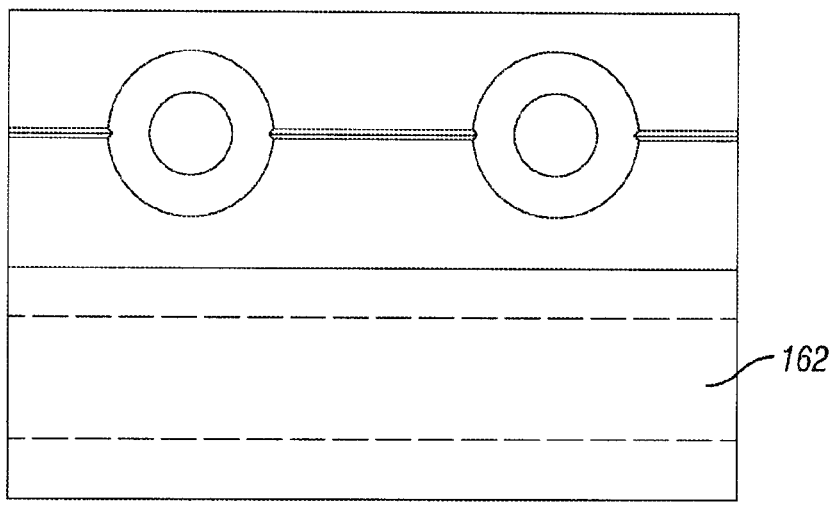
FIG. 74
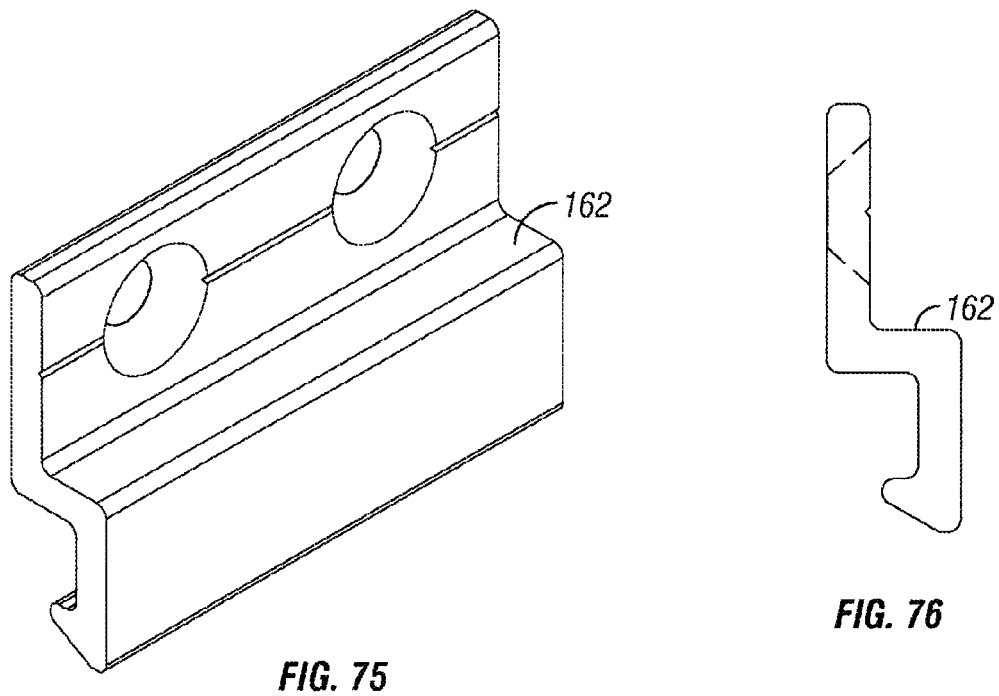
FIG. 75
FIG. 76

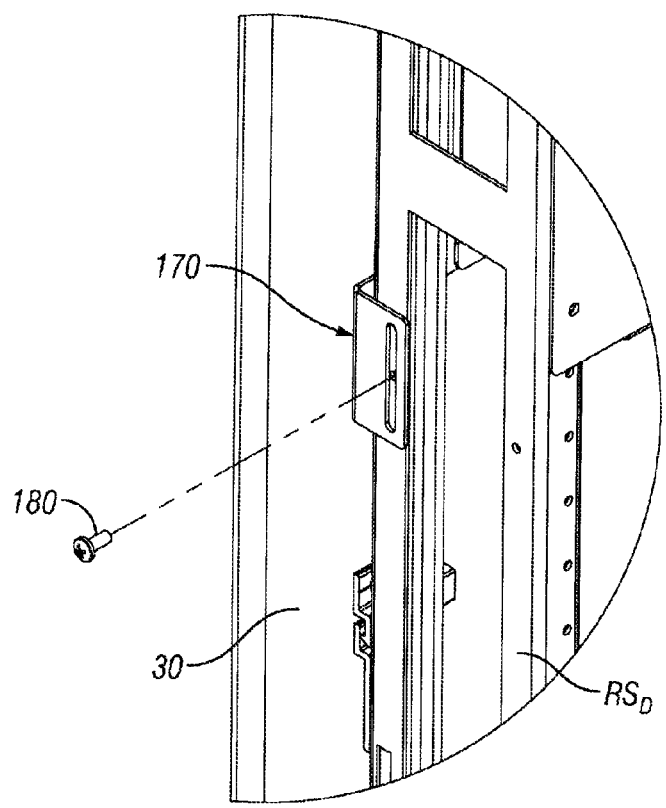
FIG. 78
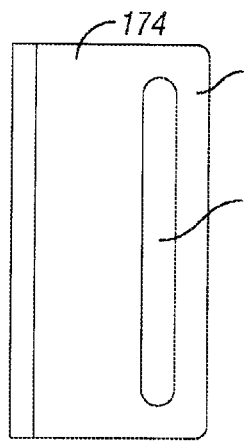 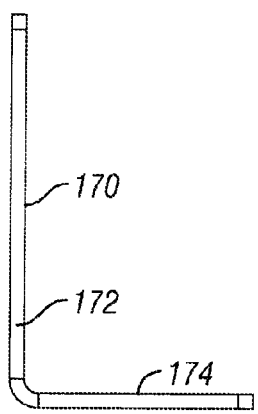 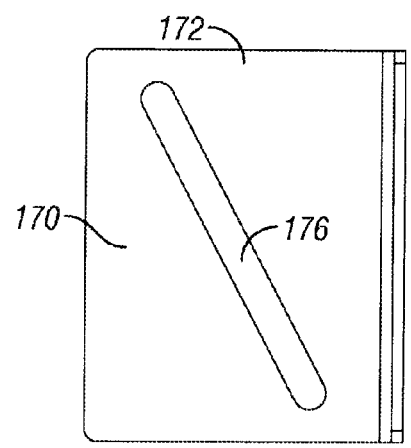
FIG. 79　　　　　FIG. 80　　　　　FIG. 81

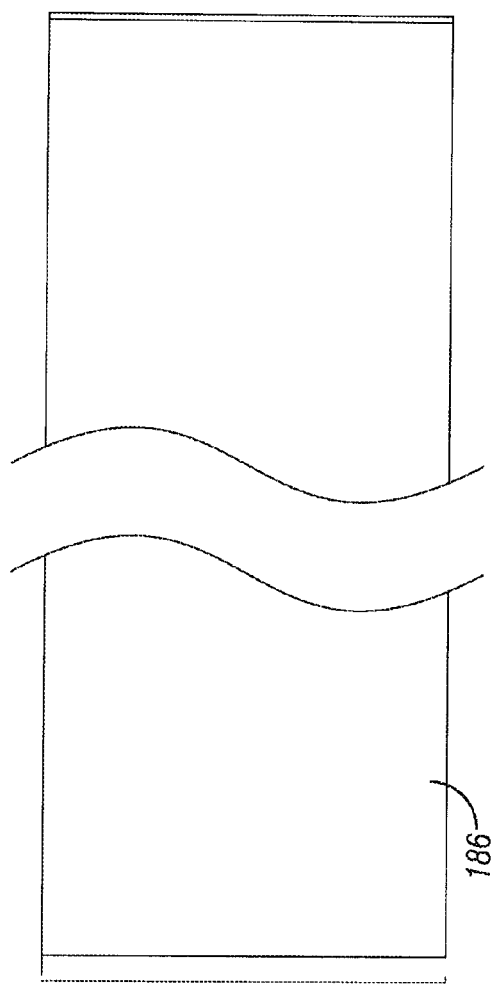
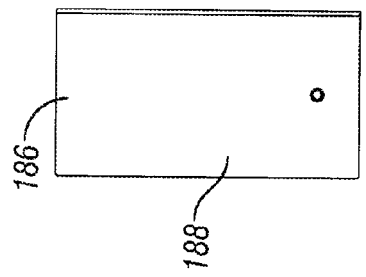
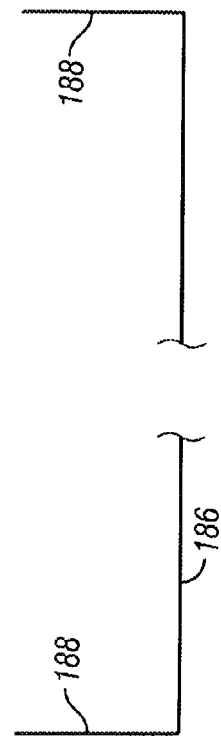
FIG. 83
FIG. 85
FIG. 84

MODULAR MEDICAL HEADWALL SYSTEM

FIELD OF THE INVENTION

The present invention relates to devices for providing medical gas and electrical services to hospitals and other medical care facilities.

BRIEF DESCRIPTION OF THE DRAWINGS

FIG. 2 is a perspective view of the adjustable base assembly of the headwall.

FIG. 3 is an end view of the base assembly shown in FIG. 2.

FIG. 5 is a bottom view of the base bottom.

FIG. 6 is an end view of the base bottom.

FIG. 7 is a fragmented elevational view of the front of the base bottom.

FIG. 8 is a fragmented plan view of the base bottom.

FIG. 40 is an enlarged fragmented front elevational view of the stud member.

FIG. 41 is an end elevational view of the stud member.

FIG. 42 is an end elevational view of two interlocked stud members showing how the hooks of one stud extend through the slots of the adjacent stud.

FIG. 49 is a plan view of the left crown molding adjustment bracket.

FIG. 50 is an inside or right side perspective view of the left crown molding adjustment bracket.

FIG. 51 is a right side elevational view of the left crown molding adjustment bracket.

FIG. 52 is a front elevational view of the left crown molding adjustment bracket.

FIG. 60 is a plan view of the crown molding header panel.

FIG. 61 is an enlarged fragmented front elevational view of the header panel shown in FIG. 60.

FIG. 62 is an end elevational view of the header panel.

FIG. 63 an enlarged fragmented rear elevational view of the header panel shown in FIG. 60.

FIG. 67 is a right side elevational view showing a cover panel being hung on the front of a headwall section.

FIG. 68 is an enlarged view of the section included in the circle designated 68 in FIG. 67 showing the panel hangers on the back of the panel and front of the headwall's stud shown just prior to engagement.

FIG. 74 is a rear elevational view of the down hook on the back of the cover panel.

FIG. 75 is a rear perspective view of the down hook on the back of the cover panel.

FIG. 76 is a side elevational view of the down hook on the rear of the cover panel.

FIG. 78 shows an enlarged view of the portion included in the circle designated 78 in FIG. 77 illustrating the panel locking bracket on the right side of the stud.

FIG. 79 is a right side elevational view of the panel locking bracket shown in FIG. 78.

FIG. 80 shows an end elevational view of the panel locking bracket.

FIG. 81 shows a front elevational view of the panel locking bracket.

FIG. 83 is a fragmented front elevational view of the trim panel for the base assembly on the floor-mounted headwall.

FIG. 84 is fragmented plan view of the trim panel for the base assembly on the floor-mounted headwall.

FIG. 85 is an end elevational view of the trim panel for the base assembly on the floor-mounted headwall.

DETAILED DESCRIPTION OF THE PREFERRED EMBODIMENT

Figure 1:
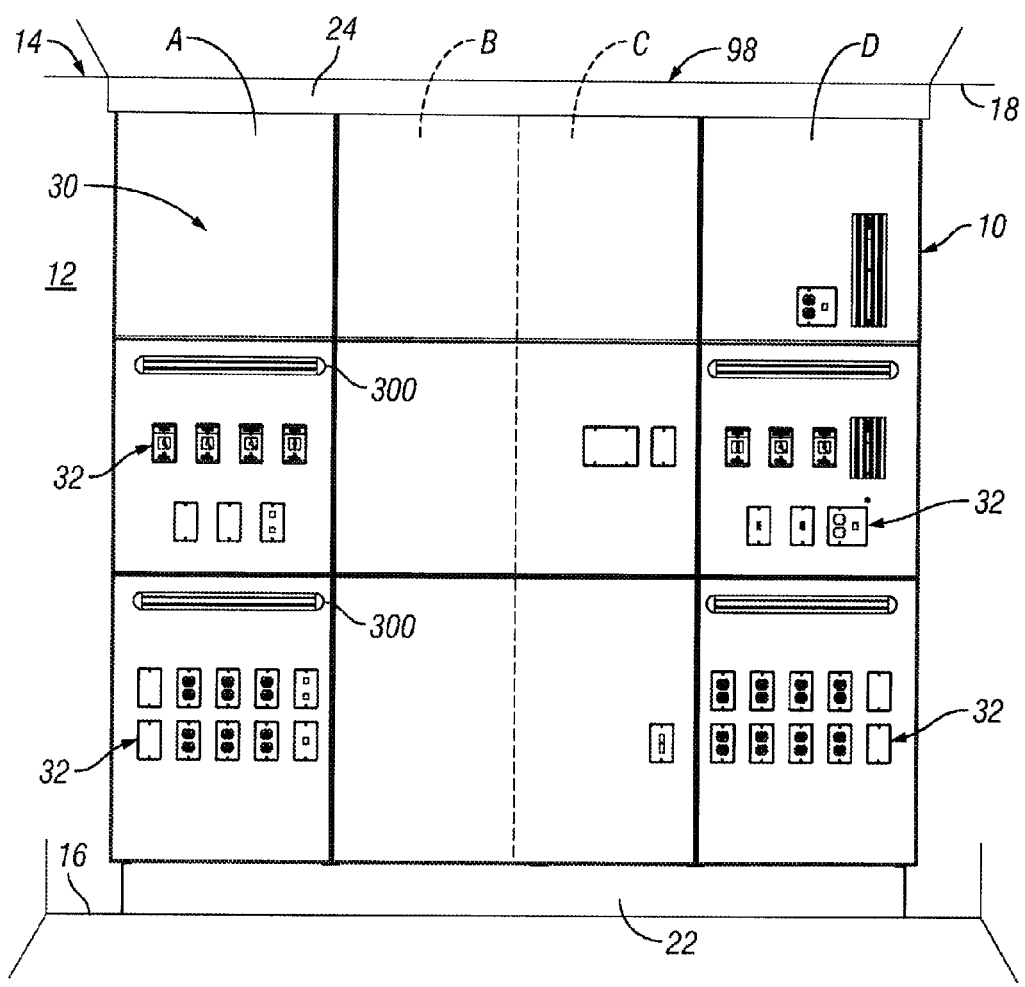
FIG. 1 is a front elevational view of a modular headwall assembly made in accordance with a preferred embodiment of the present invention.
Figure 4:
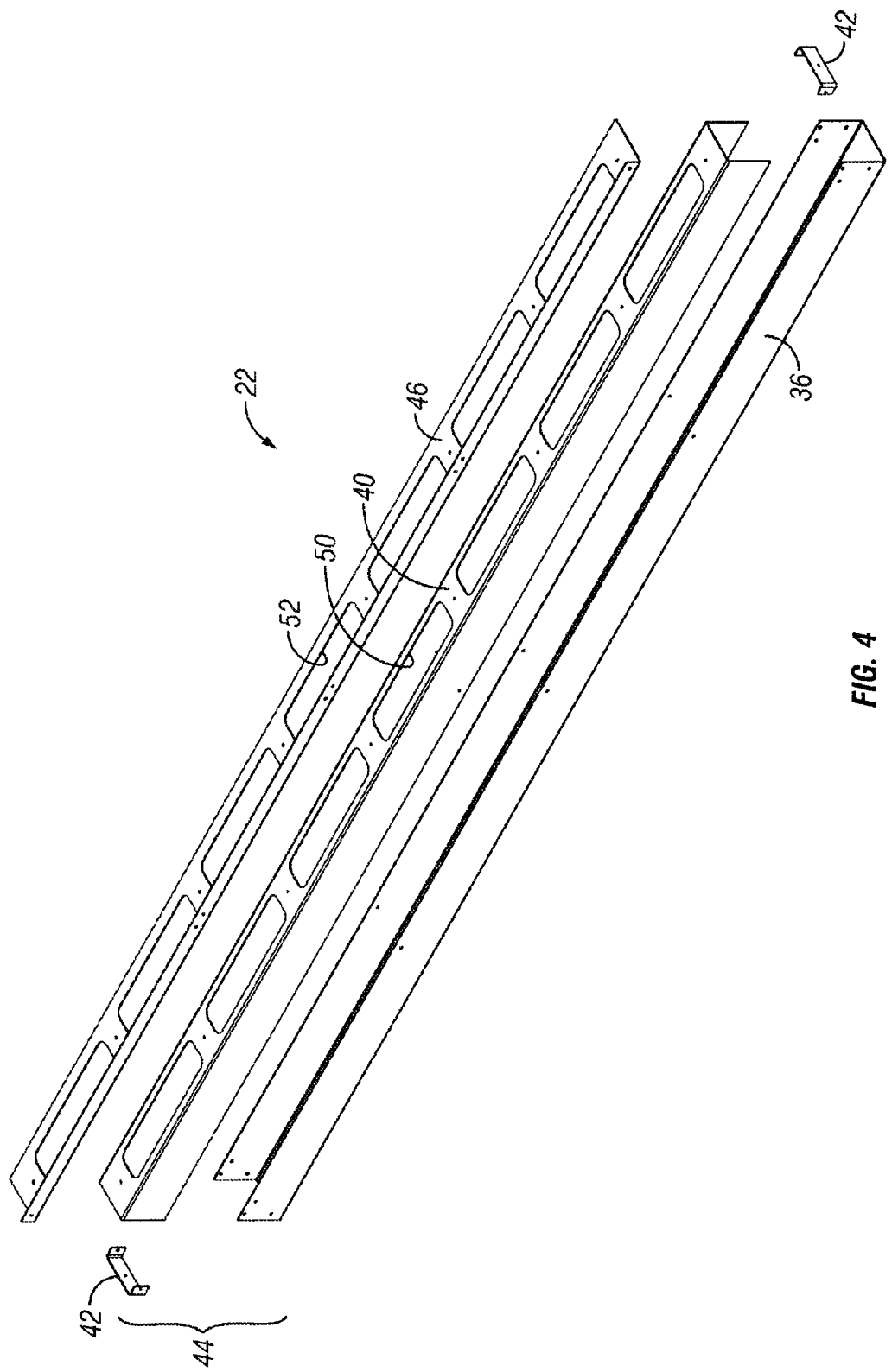
FIG. 4 is an exploded perspective view of the base assembly shown in FIG. 2.
Figure 9:
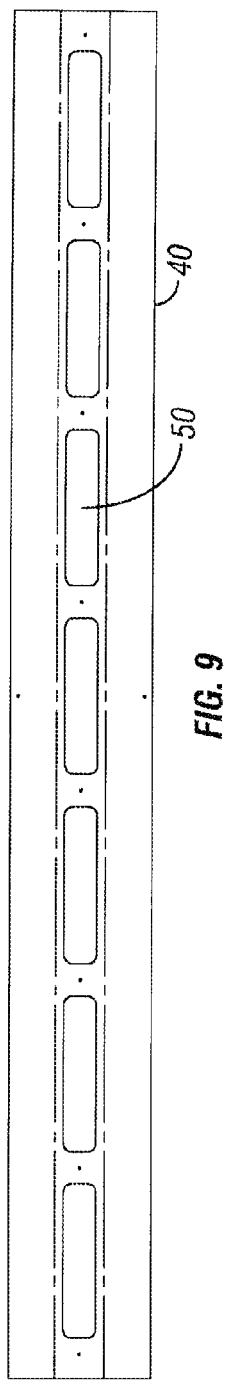
FIG. 9 is a plan view of the top member of the base assembly.
Figure 11:
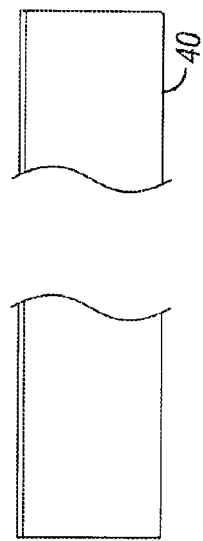
FIG. 11 is a front elevational view of the top member.
Figure 12:
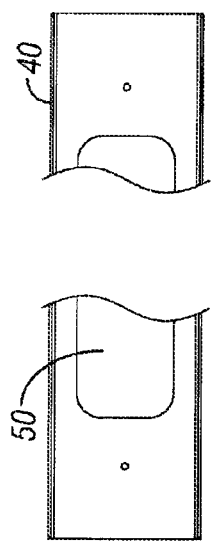
FIG. 12 is a fragmented bottom view of the top member.
Figure 10:
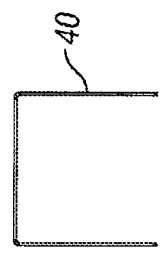
FIG. 10 is an end view of the top member.

Turning now to the drawings in general and to FIG. 1 in particular, there is shown therein a modular medical headwall system constructed in accordance with a first preferred embodiment of the present invention and designated generally by the reference numeral 10. As used herein, "medical headwall" refers to a structure which provides various medical services in a patient care area in a medical facility. "Medical service" refers to any one of a variety of gas, electrical, data, or communication services, including but not limited to oxygen, compressed air, vacuum (suction), electricity, telephone and video cable.

The headwall 10 is illustrated installed on a wall 12 in a structure 14 having a floor 16 and a ceiling 18. The headwall 10 comprises a plurality of headwall sections. In the embodiment of FIG. 1, the headwall 10 comprises first, second, third, and fourth sections, designated as A, B, C, and D. Each of the headwall sections A, B, C, and D is configured to be arranged side by side with other headwall sections to form the headwall.

The headwall 10 is supported on a base assembly 22 that is fixed to the floor 16. The headwall 10 also includes a top trim assembly, such as the crown molding assembly 24, which conceals the space between the top of the headwall and the ceiling 18 of the structure 14.

Each of the headwall sections A, B, C, and D comprises a frame (not seen in this FIG. 1), each of which may support one or more and usually a number of medical service outlets designated collectively at 32. The headwall 10 further includes a matrix of panels 30 which cover the frames except for the service outlets 32.

Figure 14:
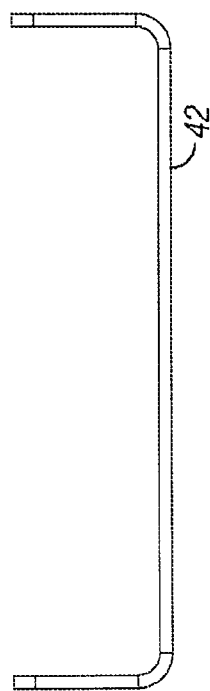
FIG. 14 is an end view of the base end bracket.
Figure 15:
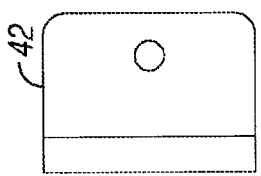
FIG. 15 is a side elevational view of the base end bracket.
Figure 13:
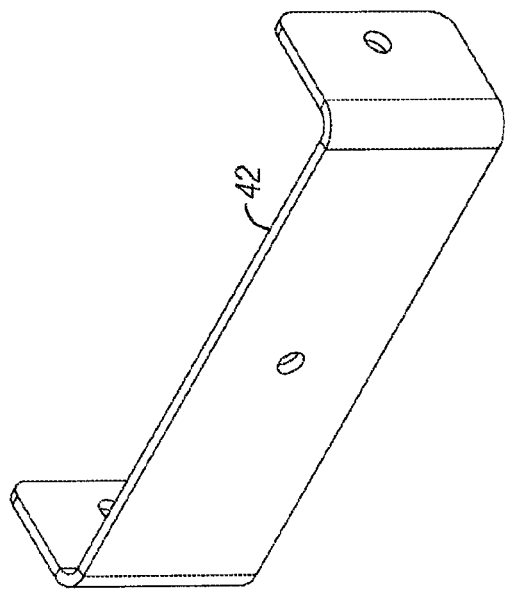
FIG. 13 is a perspective view of the end bracket of the base assembly.
Figure 16:
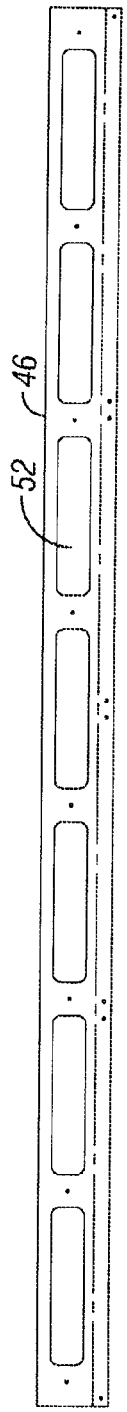
FIG. 16 is a plan view of the track member of the base assembly.
Figure 18:
FIG. 18 is a fragmented plan view of the base track.
Figure 19:
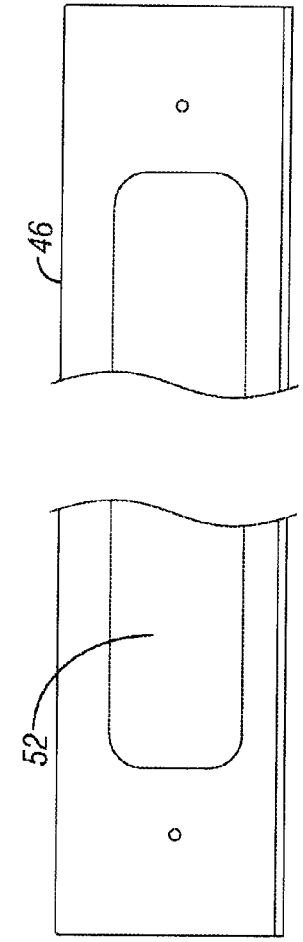
FIG. 19 is a fragmented bottom view of the base track.
Figure 17:
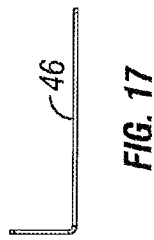
FIG. 17 is an end view of the base track.

Turning now to FIGS. 2-19, a preferred base assembly 22 will be described. In the embodiment of FIG. 1, the base assembly 22 is fixed to the floor. In accordance with the present invention, the base assembly 22 is self-leveling. More specifically, the support track is adjustably supportable on the floor rail so that when the plurality of head wall sections are arranged side by side in the support track the plurality of headwall sections can be collectively leveled regardless of irregularities in the floor. The base assembly 22 comprises a bottom member 36 (FIGS. 5-8) that may be U-shaped. One or more longitudinal slots 38 are provided along the center of the bottom 36. A top member 40 (FIGS. 9-12) having an inverted U-shape is received in the bottom member 36. The bottom edges of the top member 40 may be fixed using several pairs of screws (FIG. 3) or the like spaced along the top edges of the bottom member 36. An end plate or bracket 42 (FIGS. 13-15) may be included on each end of the bottom member 36. The assembled top and bottom members 36 and 40 form a floor rail 44.

An L-shaped horizontal support track 46, shown in FIGS. 16-19, is supported along the top of the floor rail 44. The support track 46 is configured to receive the bottom of the headwall sections A, B, C, and D in the assembled headwall system 10. The support track 46 is adjustably supportable on the floor rail 44 so that the support track can be leveled regardless of whether the floor rail is level when it is fixed to the floor 16.

The base assembly 22 preferably is the first part of the headwall system 20 to be installed. The bottom member 36 is positioned in the desired location on the floor 16 so that the back side abuts the dry wall or other interior finish. Then the bottom 36 is secured to the floor 16 with anchors (not shown) or some other suitable means. The anchors are placed in the slots 38 at those points along the floor 16 where the bottom member 36 is in contact with the floor. That is, if the floor 16 is uneven, the anchors should not be placed where a depression in the floor creates a gap between the floor and the bottom member 36. In most instances, the base assembly 22 is shipped already assembled as shown in FIGS. 2 and 3. For that reason, the top member 40 and the support track 46 may also include slots 50 and 52 so that the anchors may be placed through the assembly.

Figure 20:
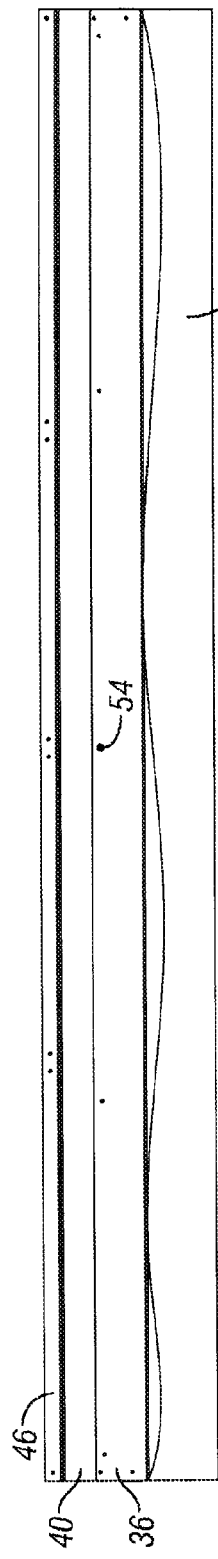
FIG. 20 is a diagrammatic illustration of the base assembly positioned on an unlevel surface.
Figure 21:
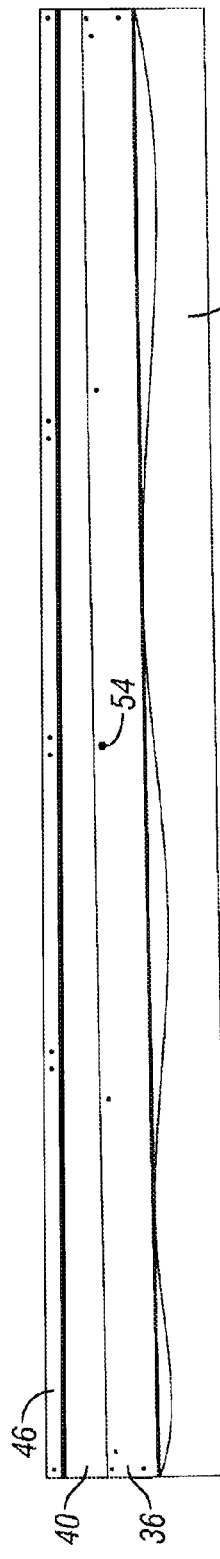
FIG. 21 is a diagrammatic illustration of the base assembly positioned on an unlevel surface where the right side of the surface and base bottom is higher than the left side and the base assembly is adjusted to level the upper member and track.
Figure 22:
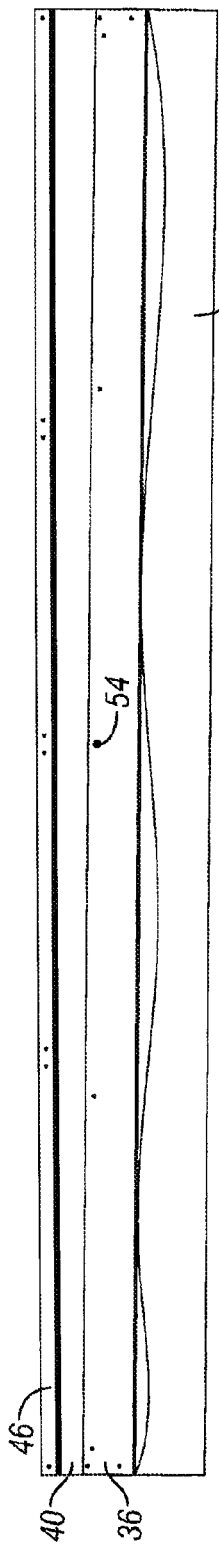
FIG. 22 is a diagrammatic illustration of the base assembly positioned on an unlevel surface where the right side of the surface and base bottom is lower than the left side and the base assembly is adjusted to level the upper member and track.
Figure 23:
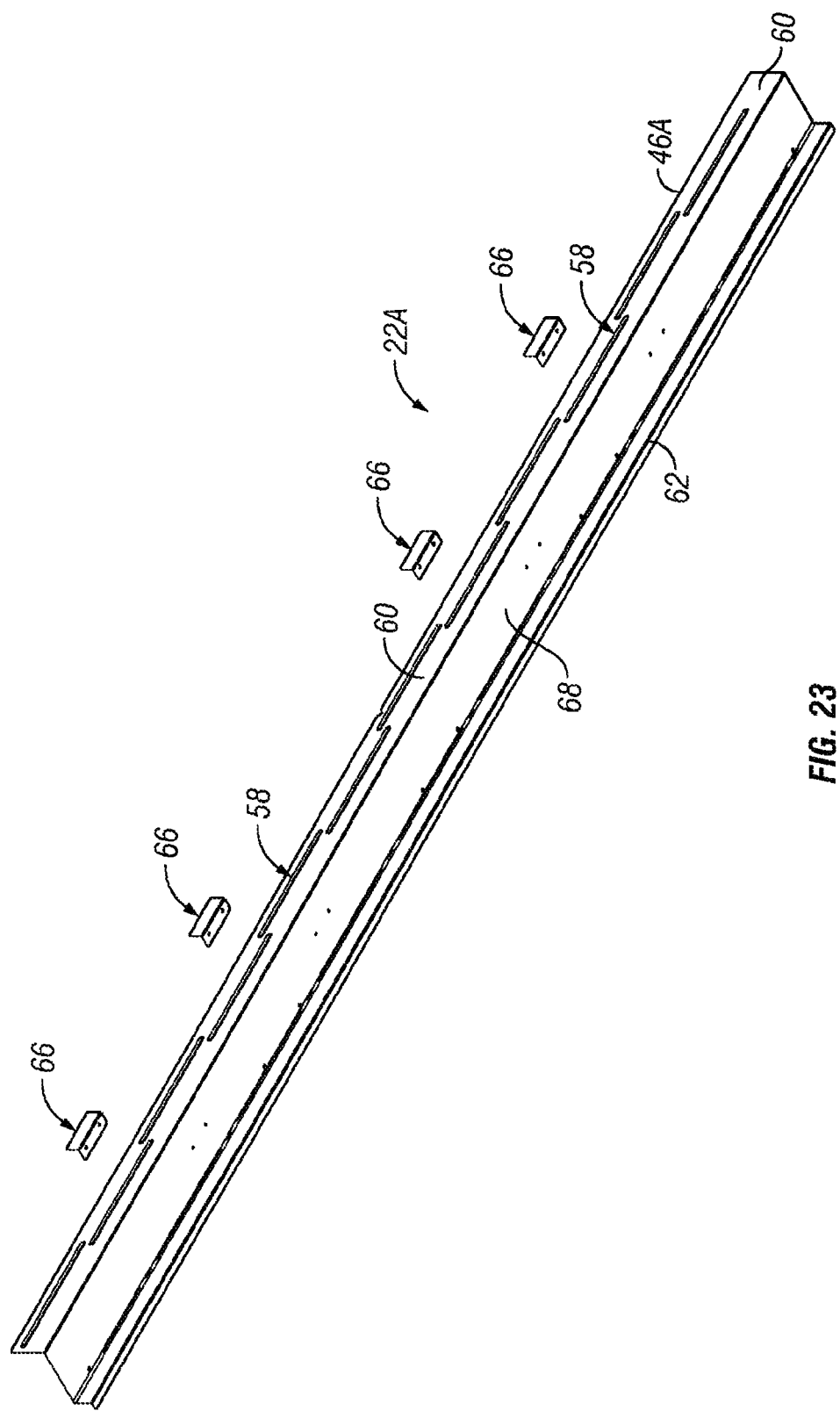
FIG. 23 is an exploded perspective view of a hanging base assembly for use with a headwall that attached to the wall a distance above the floor.
Figure 25:
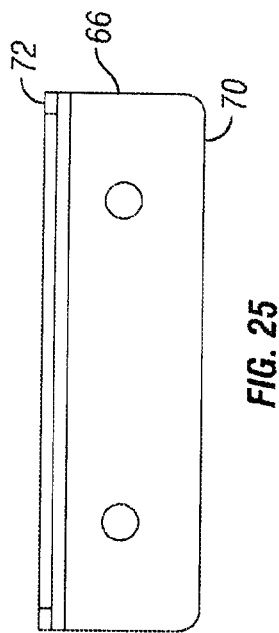
FIG. 25 is a bottom view of the safety catch of the hanging base assembly.
Figure 27:
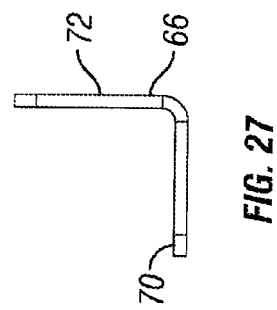
FIG. 27 is an end elevational view of the safety catch of the hanging base assembly.
Figure 24:
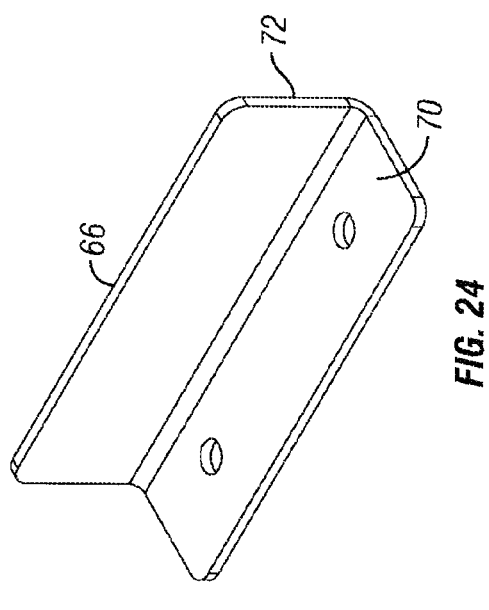
FIG. 24 is a perspective view of the safety catch of the hanging base assembly.
Figure 26:
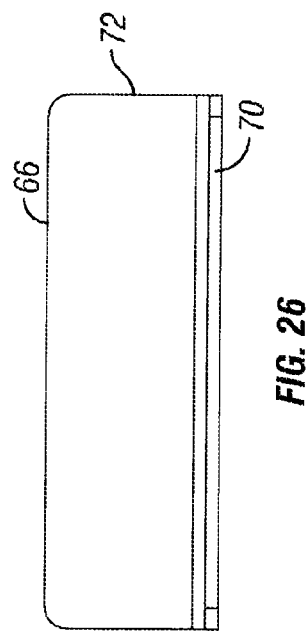
FIG. 26 is a rear view of the safety catch of the hanging base assembly.
Figure 28:
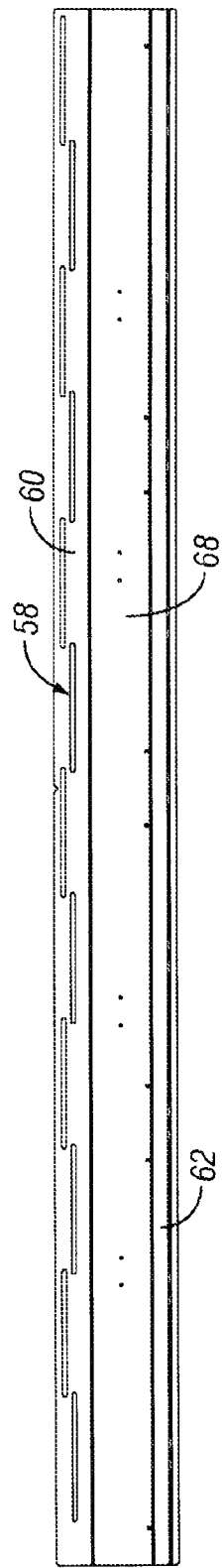
FIG. 28 is a front elevational view of the track member of the hanging base assembly.
Figure 31:
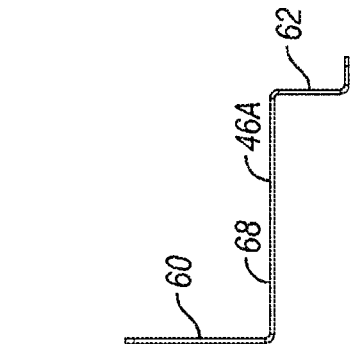
FIG. 31 is an enlarged end view of the track member shown in FIG. 28.
Figure 30:
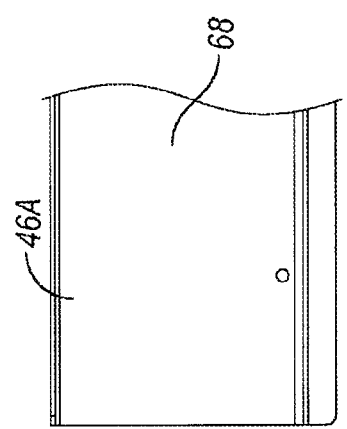
FIG. 30 is an enlarged fragmented plan view of the track member shown in FIG. 28.
Figure 29:
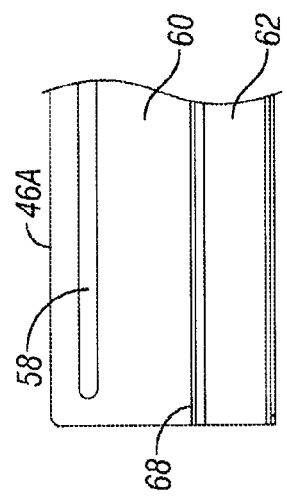
FIG. 29 is an enlarged fragmented view of the track member shown in FIG. 28.

Once the floor rail 44 is secured to the floor, the support track 46 is leveled. As indicated, the top member 40 may be secured to the bottom member 36 with screws. Preferably, one pair of screws 54 is centered. With only the center set of screws 54 installed in the floor rail 44, and the support track 46 secured along its length to the top member 40, the rail can be leveled as needed by tilting or pivoting the rail to one side or the other. This is illustrated in the FIGS. 20-22. In FIG. 20, the floor 16 is uneven but level. In FIG. 21, the floor 16 is higher on the right end and the bottom member 36 is lower on the left end. The support track 46 is leveled by lifting the left end of the top member 40 and track 46. In FIG. 22, the floor 16 is higher on the left end and the bottom member 36 is lower on the right end. The support track 46 is leveled by lifting the right end of the top member 40 and track 46.

In some instances the headwall system 10 will be installed "floating" on the wall 12. That is, the headwall 10 may not reach the floor 16. In these cases, the base assembly does not need the above described leveling feature. Rather, the base assembly may take the form of the hanging base assembly 22A shown in FIGS. 23-31. The hanging base assembly 22A may comprise a support track 46A (FIGS. 28-31) that is attachable directly to the wall 12 using screws (not shown) inserted through the slots 58 in an upwardly extending back flange 60. An angled lower flange 62 may be included for supporting trim. One or more safety catches 66 (FIGS. 24-27) may be attached with screws (not shown) to the flat center member 68 of the track 46A. These safety catches 66 will prevent the bottom of the headwall sections from moving off the track. Although the form of the catch may vary, the preferred catch 66 is a short angled member with a bottom flange 70 that attaches to the center member 68 of the track 46A and an upwardly extending flange 72 that engages the bottom of the headwall section.

Figures 32, 33:
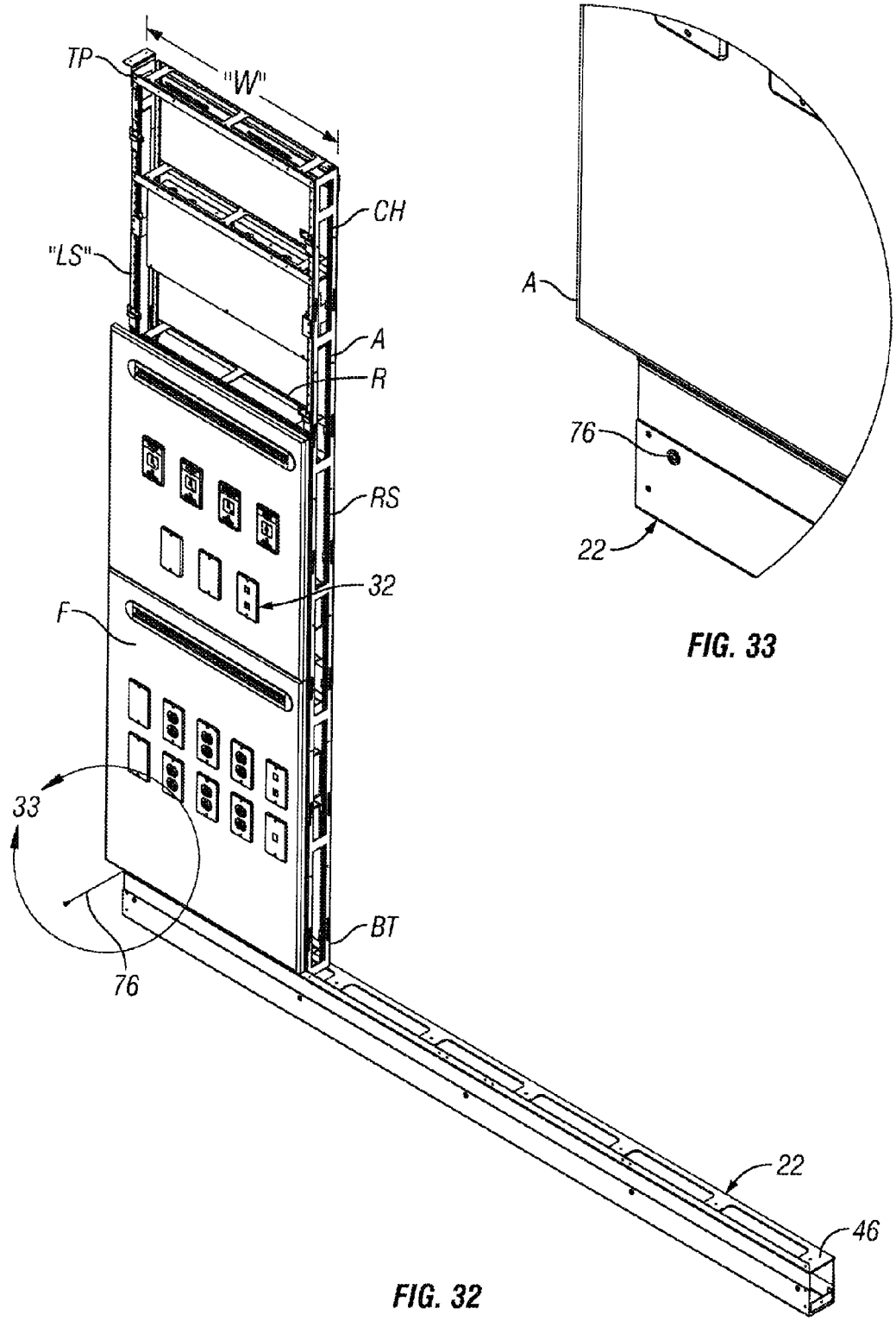
FIG. 32 is a perspective view of the adjustable base assembly with a first left wing section of the headwall position on the track member.
FIG. 33 is an enlarged view of the portion included in the circle "33" in FIG. 32.

Returning now to the floor-mounted embodiment of FIGS. 1-19, once the base assembly 22 has been secured and leveled, the first headwall or left wing section A is positioned at the left end of the support track 46, as shown in FIG. 32, and secured with one or more screws 76.

FIG. 32 also illustrates a preferred general structure for all the headwall sections. As shown, the headwall section A generally comprises a frame or chassis "CH" formed by a pair of side uprights referred to herein as the left stud LS and the right stud RS. As used herein, "left," "right," "front," "back" (or rear), "top," and "bottom" all are relative terms and refer to the view of the headwall shown in FIG. 1. One or more cross rails "R" extend horizontally between the studs LS and RS. The chassis CH has a width "W" being the dimension from the left stud LS to the right stud RS. Each headwall section also has a top "TP" and a bottom "BT." The medical service outlets 32 are mounted in the chassis CH for access from the front of the section designated generally at "F.".

Figures 34, 35:
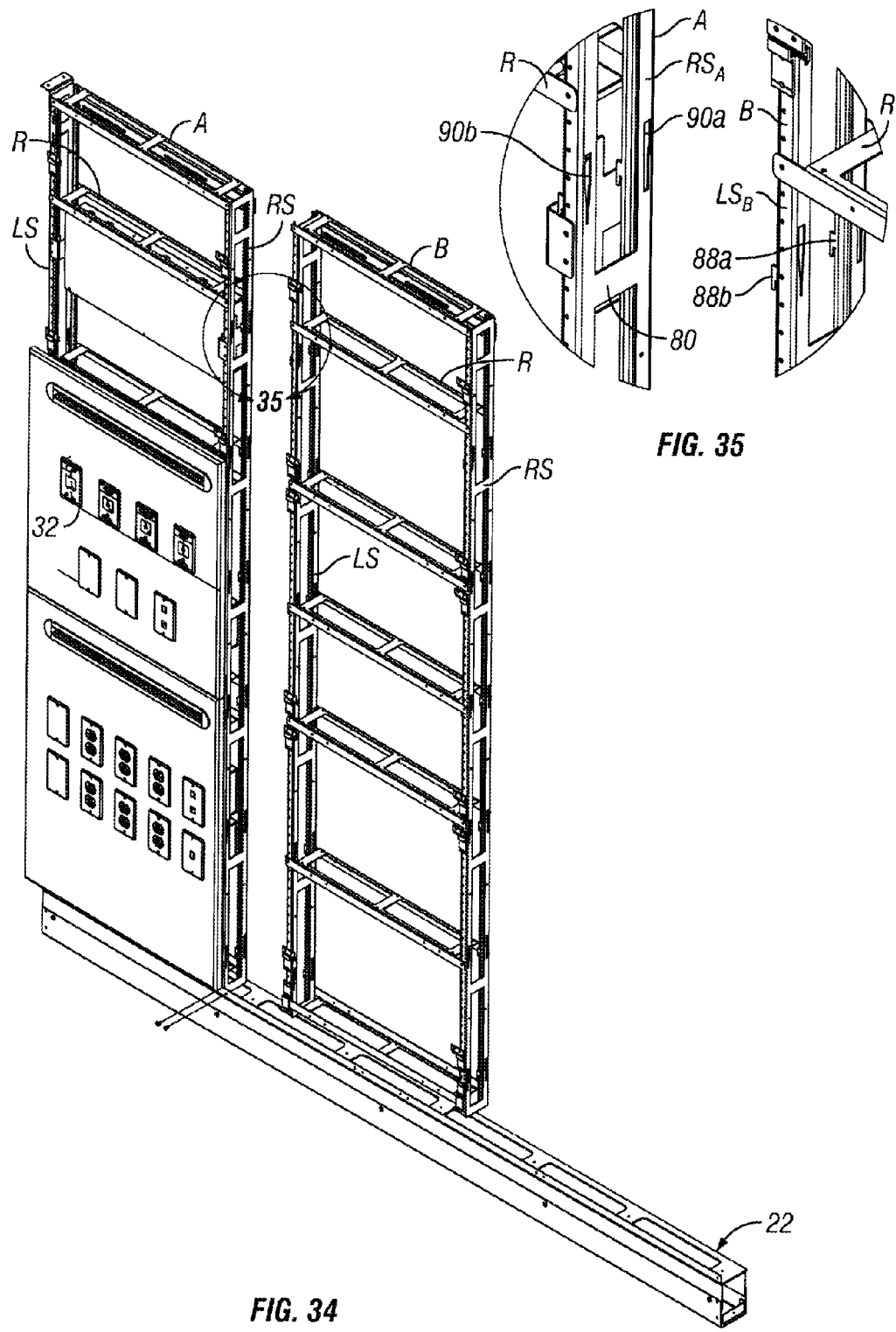
FIG. 34 is a perspective view of the adjustable base assembly with a second headwall section positioned near the left section.
FIG. 35 is an enlarged view of the portion included in the circle "35" in FIG. 32 and showing the hook-and-slot attachment system.
Figure 36:
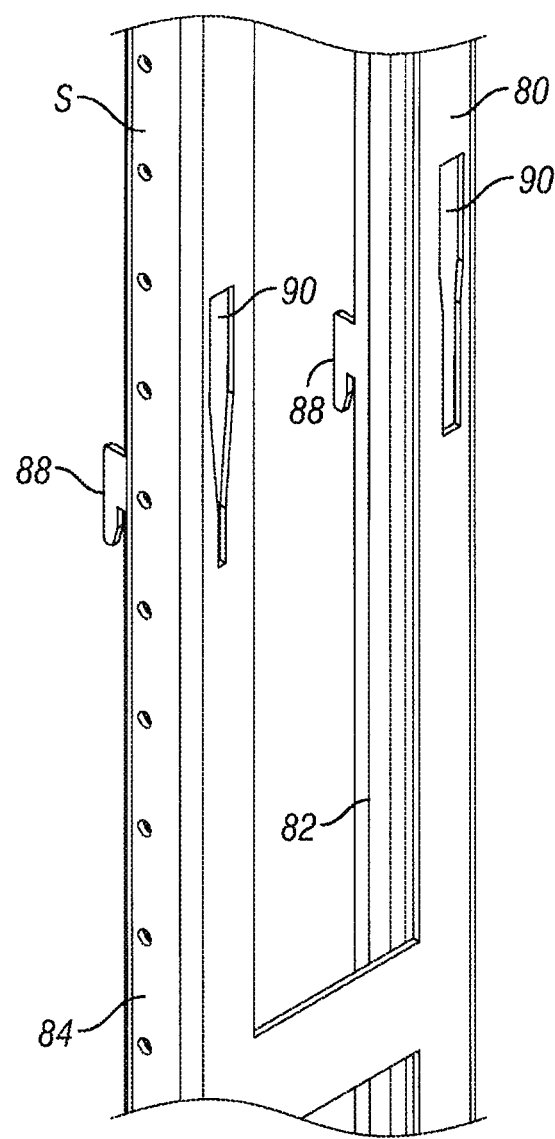
FIG. 36 is an enlarged fragmented perspective view of the outside of the stud member forming part of the frame of each headwall section and illustrating the keyhole shaped slots on the vertical members.
Figure 37:
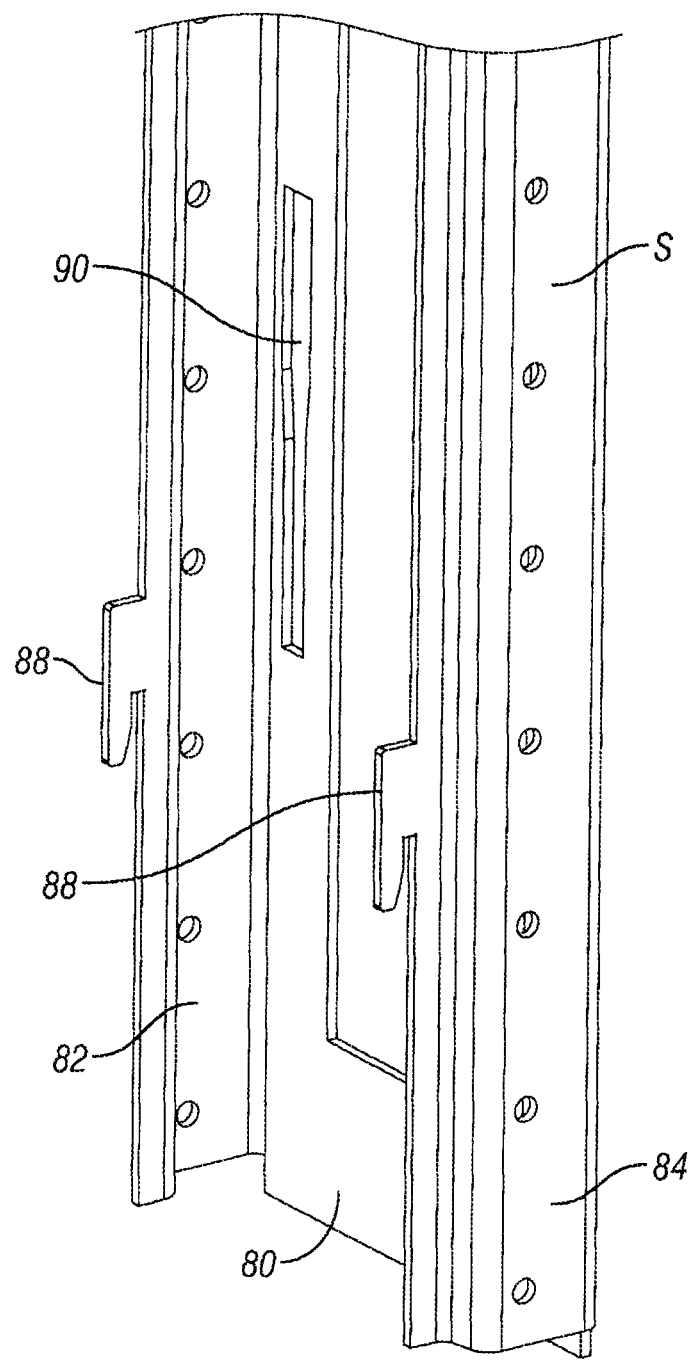
FIG. 37 is an enlarged fragmented perspective view of the inside of the stud member and illustrating the hooks on the vertical members.

Having secured the first headwall section A, or the left wing section, to the base assembly 22, the second head wall section B next is installed, as seen in FIG. 34. In this particular embodiment, the second headwall section B includes no medical service outlets. The second headwall section B also will be secured to the base assembly 22. However, in this most preferred embodiment, the second and subsequent headwall sections also are interconnected with each other. To that end, the studs of the headwall sections are provided with interlocking hooks and slots that will be explained with reference to FIGS. 35-42.

Figures 38, 39:
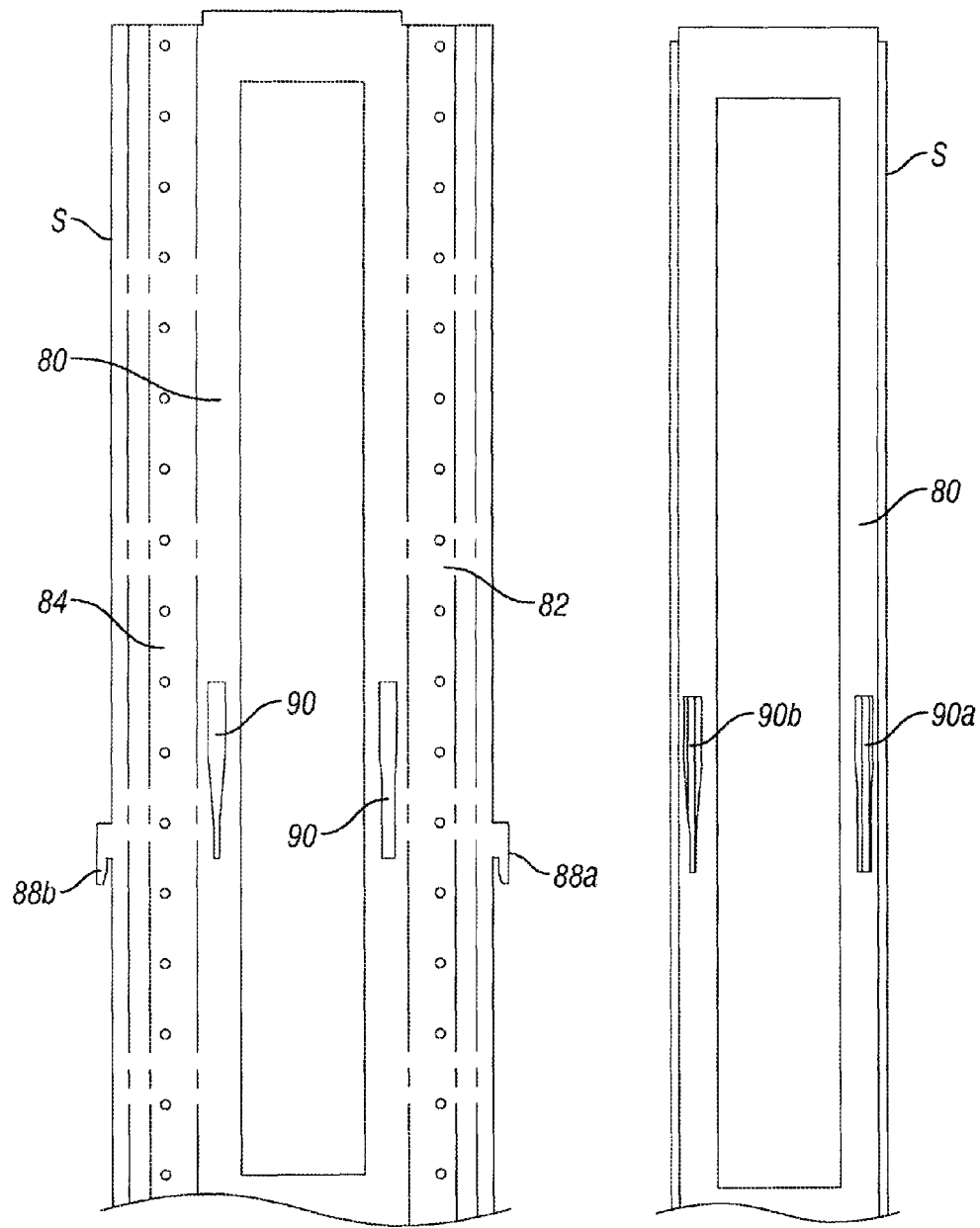
FIG. 38 is an enlarged fragmented view of the blank used to form the studs of the head walls.
FIG. 39 is an enlarged fragmented side elevational view of the stud.

Ideally, all the studs, both left and right, in all the headwall sections A, B, C, and D will be formed identically, as this simplifies manufacture and assembly. In most instances, the studs will be formed by first cutting a blank and then pressing the blank into the desired profile. An enlarged portion of the preferred blank configuration is shown in FIG. 38. FIGS. 39-41 illustrate the preferred profile. The resulting stud "S" is generally C-shaped as best seen in FIG. 41, having a planar center section 80 and perpendicularly extending side sections 82 and 84.

Along the edges of the blank (FIG. 38), tabs or hooks are formed. These are designated generally as 88. Preferably, the hooks 88 are pointed downward. Keyhole shaped slots 90 are formed in the blank so as to be positioned in the flat central section 80. The slots are positioned so that the tabs 88 on one stud are aligned with the slots 90, respectively, of the adjacent stud. In this way, as the section B is placed into the base assembly 22, as shown in FIGS. 34 and 35, the hooks 88 are guided into the upper ends of the slots 90 and the section is lowered so that the hooks slide down into the narrow lower portion of the slots. FIG. 42 shows the right stud of Section A, $RS_A$, interlocked with the left stud of Section B, $LS_B$. Now it will be apparent that the hook and slot engagement ensures that the right stud of headwall Section A, $RS_A$, is secured in abutting relation to the left stud of headwall section B, $LS_B$. Additionally, this interlocking engagement ensures that the headwall sections are aligned vertically and horizontally. The studs also may be secured to the wall studs (not shown) with screws.

Figure 43:
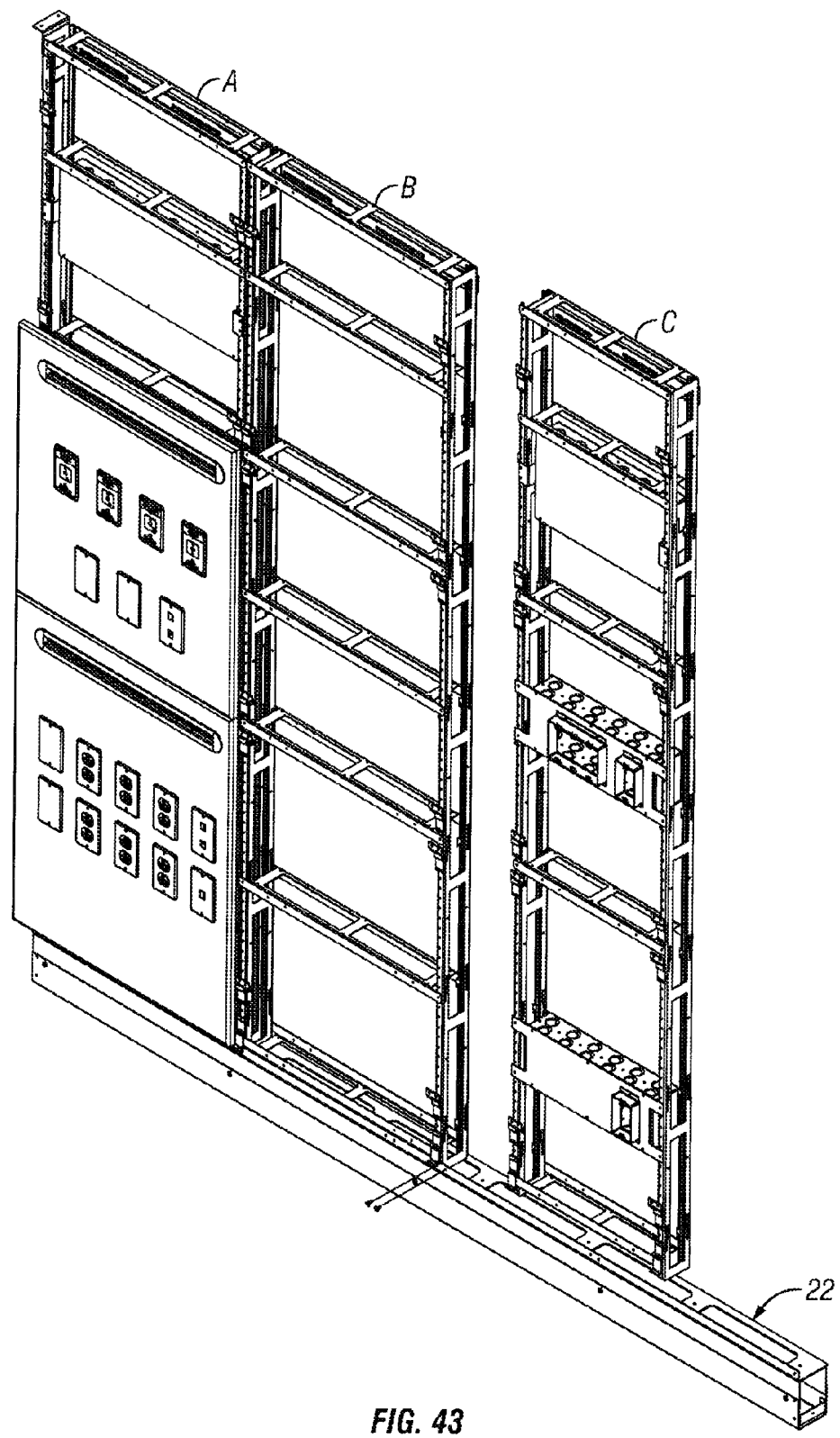
FIG. 43 is a perspective view of the adjustable base assembly with a third headwall section positioned near the second section.
Figure 44:
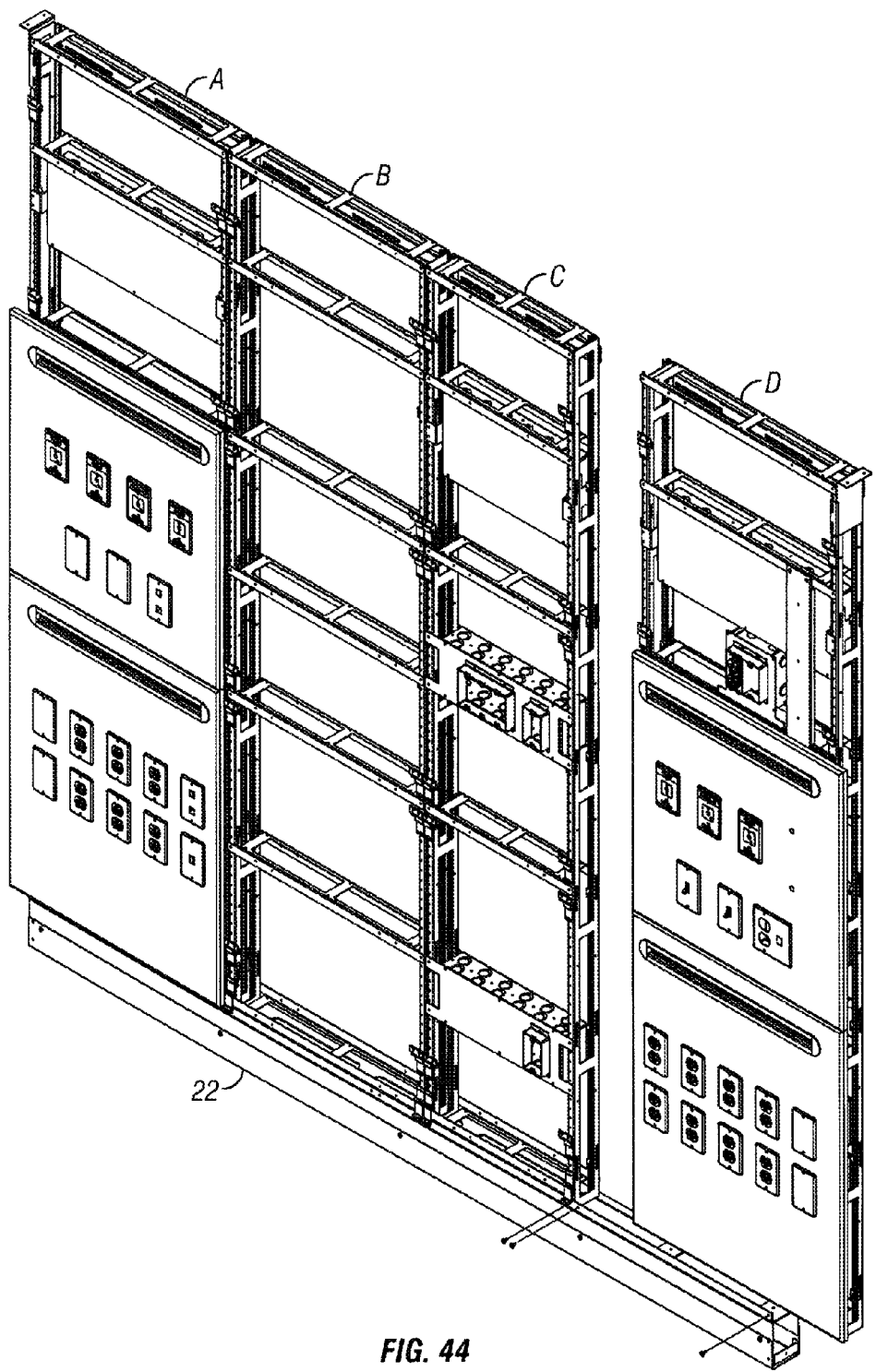
FIG. 44 is a diagrammatic illustration of a four section headwall and illustrating the orientation of the studs in each of the four sections.

The third headwall section C and the fourth or right wing section D are installed in the same manner, as shown in FIGS. 43 and 44. It will be understood that the number of the sections may vary. Additionally, the dimensions of each headwall section may vary. Still further, the number, type, and arrangement of medical service outlets may vary. Some of the headwall sections may be shipped to the site with one or more of the cover panels 30 attached. In most instances, at least some of the cover panels 30 will be installed after the headwall sections are assembled and secured to the wall 12.

Figure 45:
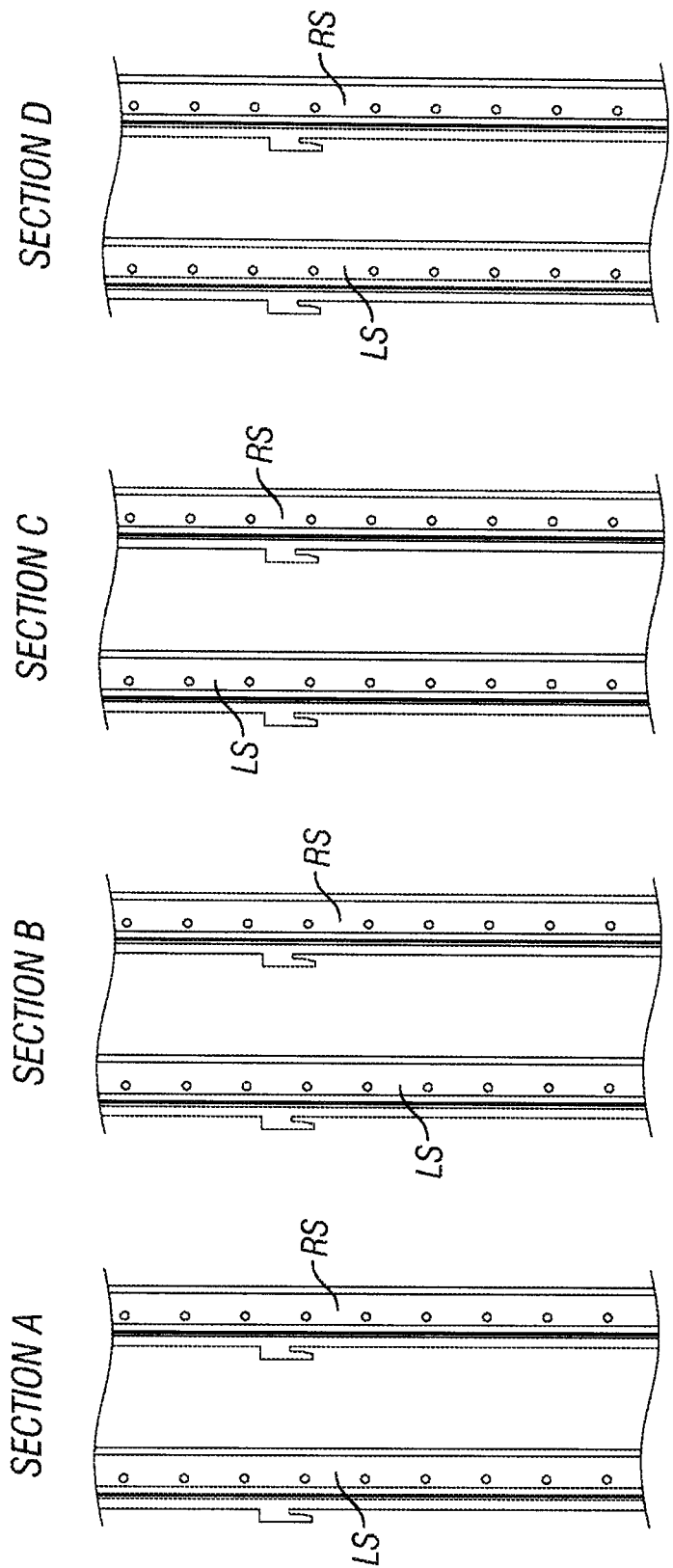
FIG. 45 is a perspective view of the adjustable base assembly with a further right wing headwall section positioned near the third section.

As indicated previously, it is advantageous for all the studs to be similarly formed. However, it is desirable to selectively orient the studs so as to facilitate the addition of side trim, described in more detail hereafter. As shown in FIG. 45, all the right side studs in the 4-section headwall shown and described herein are oriented with the hooks 88 extending inwardly (towards the inside of the chassis CH) so that the slots (not seen in this figure) are exposed. Except for the left stud on the first section A, all of the left studs are oriented so that the hooks 88 extend outwardly toward the adjacent headwall section. The left stud on the first headwall section A is also oriented with the hooks 88 directed inward. This arrangement works for systems in which the headwall sections are installed left to right. It will be appreciated that the system could be configured for installation right to left, and the arrangement of the hooks and slots would be reversed.

Figure 46:
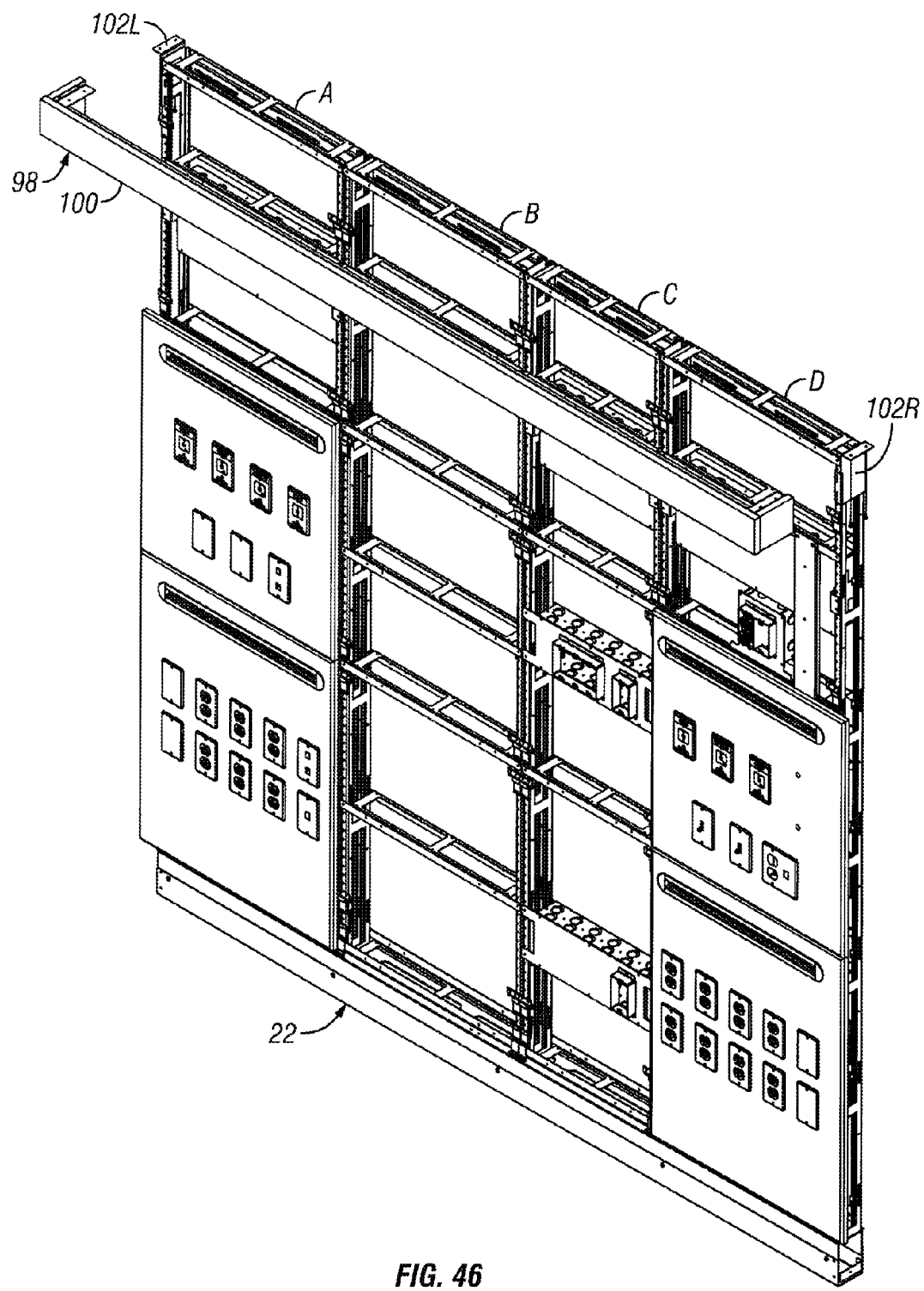
FIG. 46 a partially exploded view showing the addition of the crown molding assembly for the partially assembled headwall.

Having secured all the headwall sections A, B, C, and D in position, the trim assemblies may be attached. FIG. 46 illustrates the addition of a preferred upper trim assembly 98 for use with a headwall system 10 that reaches the ceiling 18. This trim assembly 98 comprises a cornice or crown molding trim panel 100 that abuts the ceiling 18 (FIG. 1). More preferably, the crown molding trim panel 100 is adjustably connectable to the top of the headwall 10 so that the trim panel can be positioned to about the ceiling 18 even when the ceiling line is not level.

Figure 47:
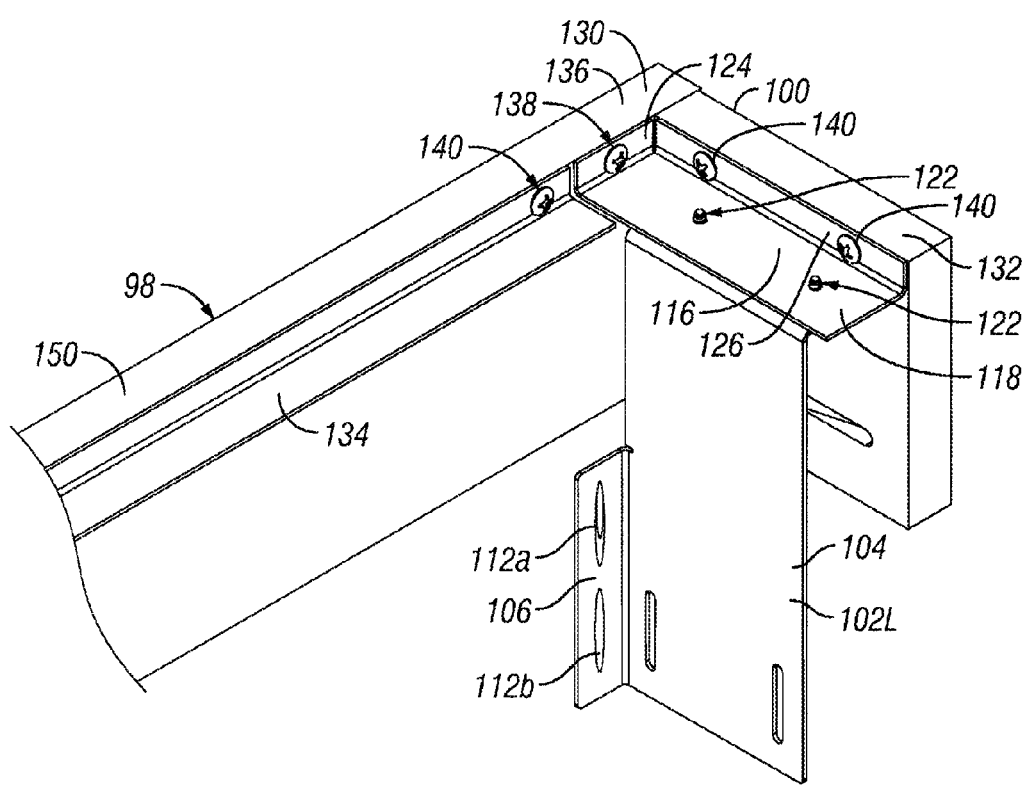
FIG. 47 is an enlarged fragmented perspective view of the inside left corner of the crown molding assembly of the headwall.
Figure 48:
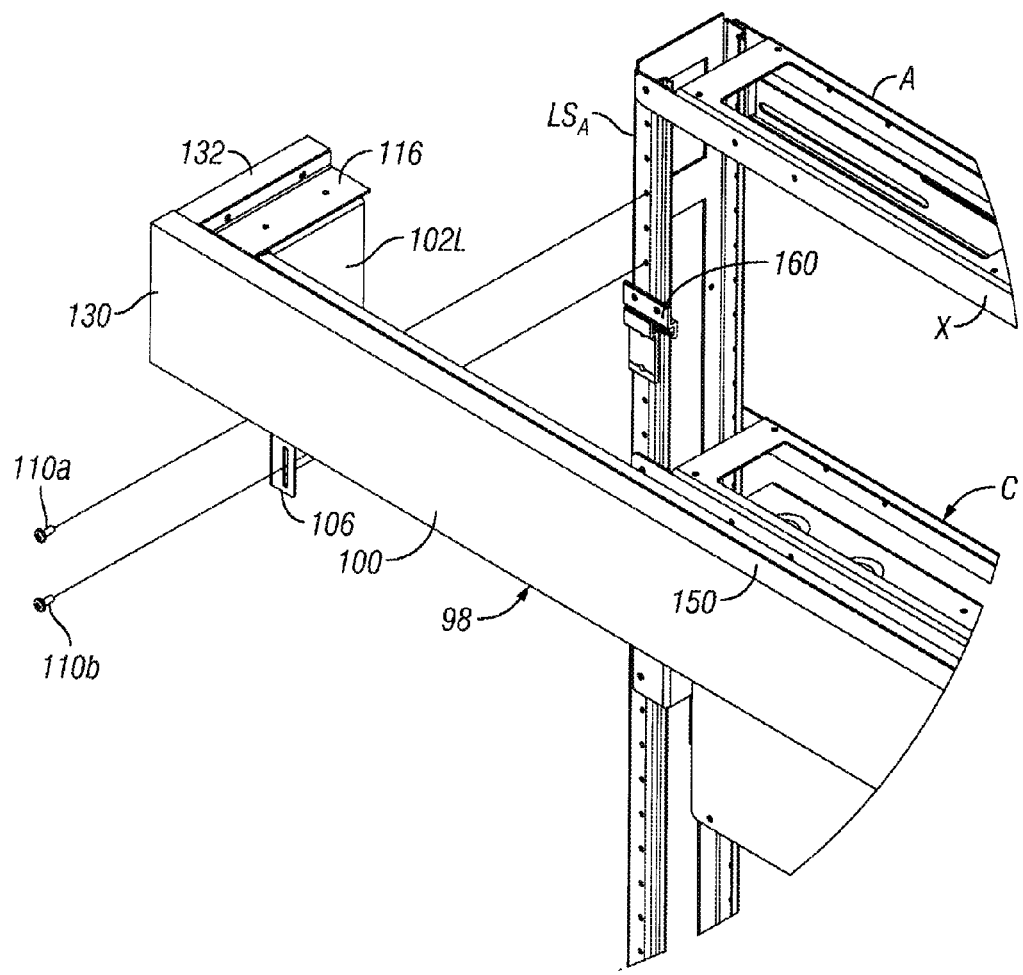
FIG. 48 is an enlarged fragmented perspective view of the outside left corner of the crown molding assembly of the headwall.
Figure 54:
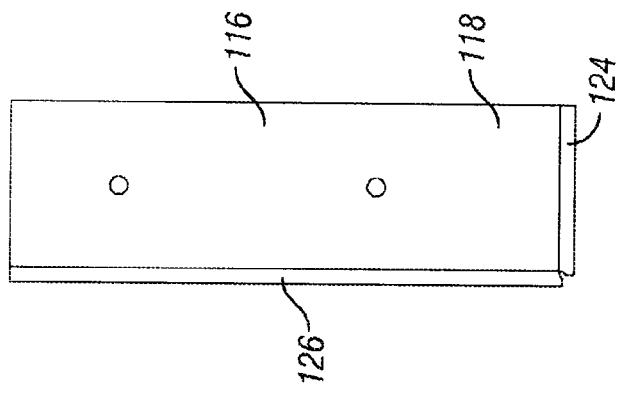
FIG. 54 is a plan view of the crown molding support bracket.
Figure 56:
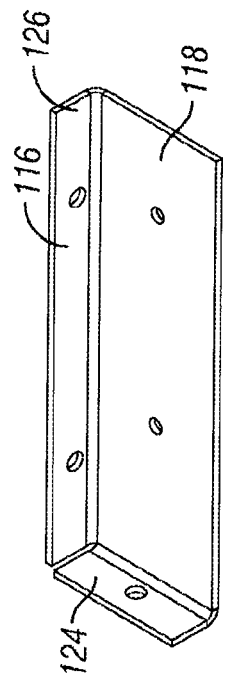
FIG. 56 is an upper perspective view of the crown molding support bracket.
Figure 53:
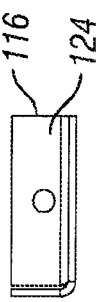
FIG. 53 is a front elevational view of the crown molding support bracket.
Figure 55:
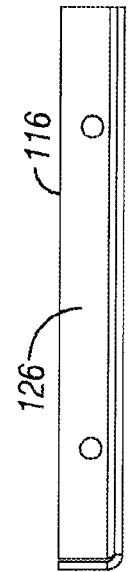
FIG. 55 is a right side elevational view of the crown molding support bracket.

Referring now to FIGS. 47-66, a preferred crown molding trim assembly 98 will be described in detail. The trim assembly 98 is supported on the top of the headwall 10 by a pair of crown molding adjustment brackets 102L and 102R (FIG. 46), one on the left and one on the right, as seen in FIG. 46. Enlarged end views of the trim assembly 100 are shown in FIGS. 47 and 48. The adjustment bracket 102L is shown in FIGS. 49-52. The adjustment bracket body 104 is sized to fit on the top of the stud, as seen in FIG. 46. A slotted flange 106 extends inwardly from the bottom of the body 104, and an attachment flange 108 extends inwardly from the top of the body. The adjustment bracket 102L is first attached to the stud with screws 110a and 110b (FIG. 48) through the slots 112a and 112b. The screws are not tightened completely to allow for adjustment later.

A crown molding support bracket 116, shown in FIGS. 53-56, attaches the crown molding trim panel 100 to the adjustment bracket 102L. Specifically, the body 118 of the support bracket 116 is attached to the attachment flange 108 (FIG. 50) of the adjustment bracket 102L using screws 122 (FIG. 47). The planar body 118 of the support bracket 116 has a small front flange 124 and a side flange 126.

Figure 57:
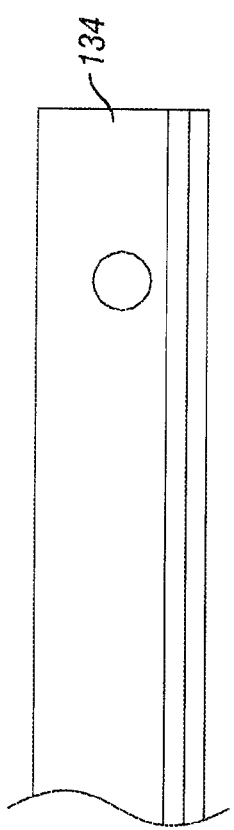
FIG. 57 is a rear elevational view of the crown molding header support bracket.
Figure 58:
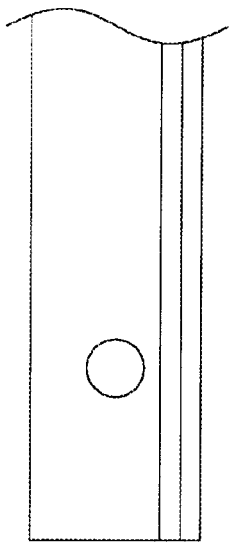
FIG. 58 is a plan view of the crown molding header support bracket.
Figure 59:
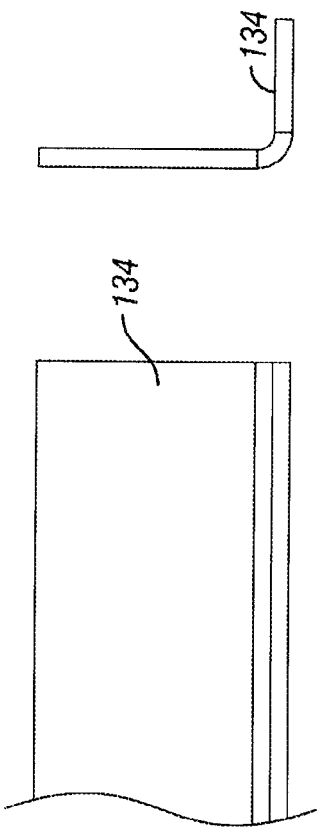
FIG. 59 is an end elevational view of the crown molding header support bracket.
Figure 66:
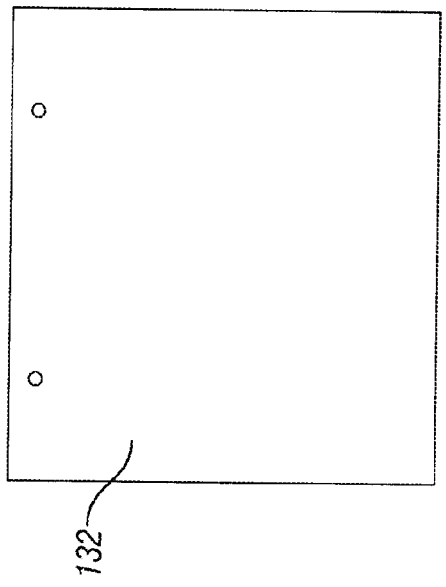
FIG. 66 is a rear elevational view of the crown molding end panel.
Figure 65:
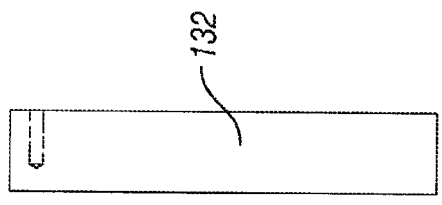
FIG. 65 is an end elevational view of the crown molding end panel.
Figure 64:
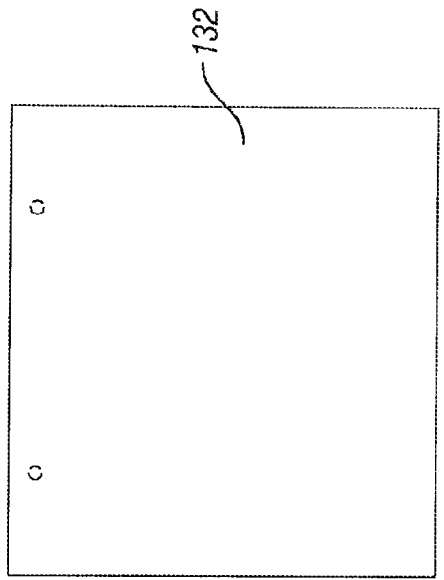
FIG. 64 is a front elevational view of the crown molding end panel.
Figure 69:
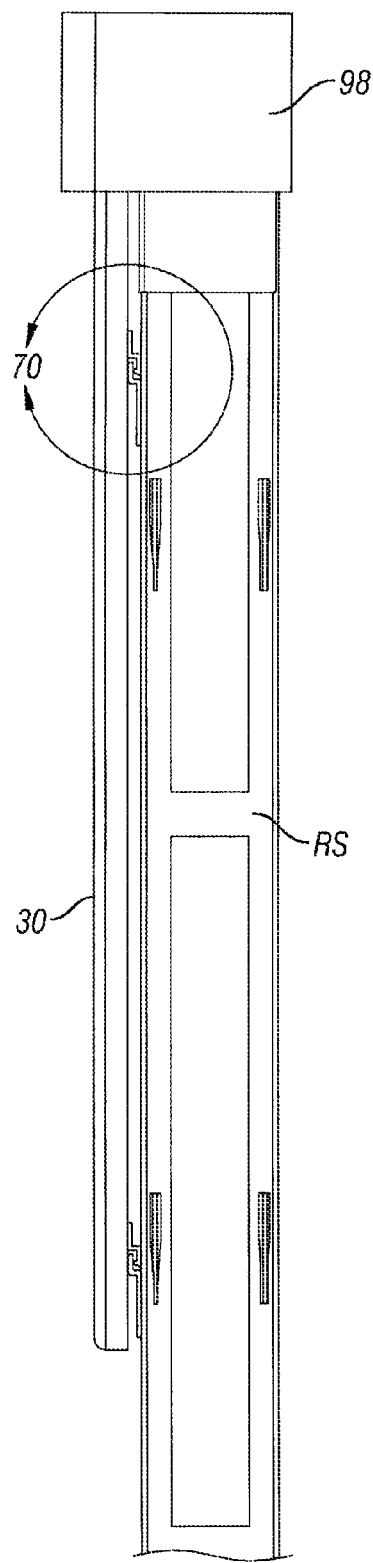
FIG. 69 is a right side elevational view showing a cover panel positioned on the front of a headwall section.
Figure 70:
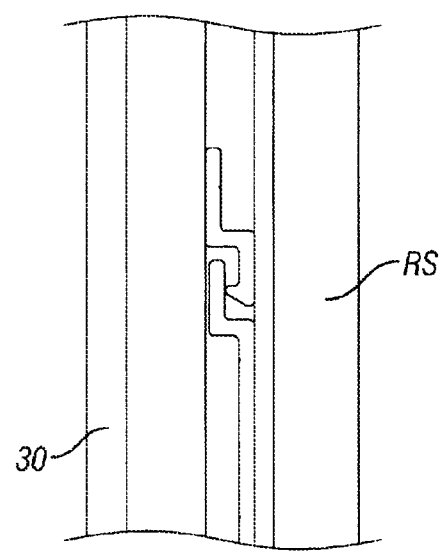
FIG. 70 is an enlarged view of the section included in the circle designated "70" in FIG. 69 showing the engaged panel hangers.
Figure 73:
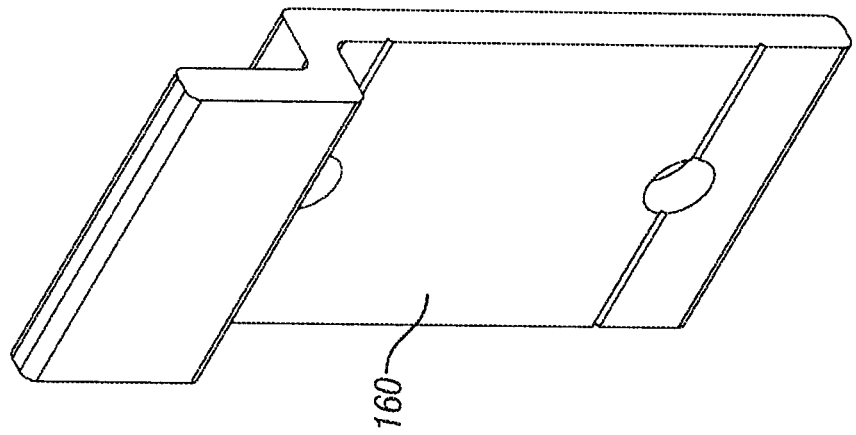
FIG. 73 is a frontal perspective view of the up hook on the stud.
Figure 72:
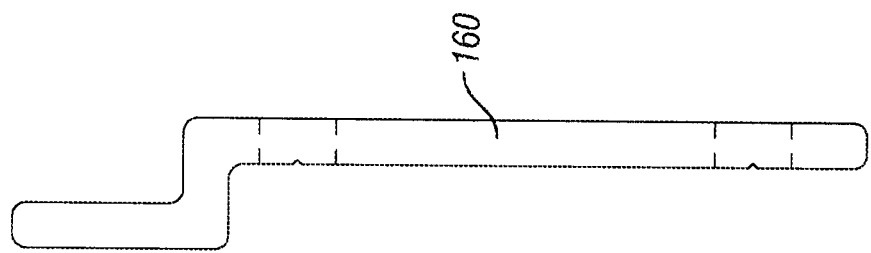
FIG. 72 is a side elevational view of the up hook.
Figure 71:
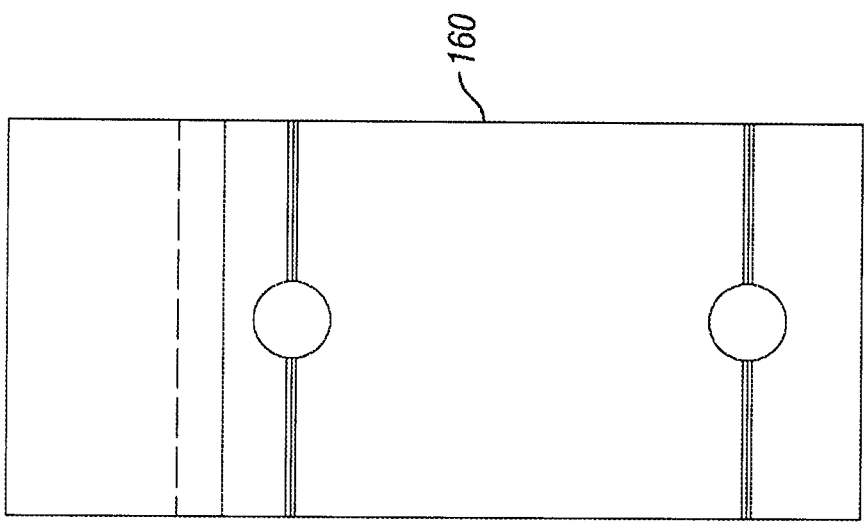
FIG. 71 is front elevational view of the up hook on the stud.
Figure 77:
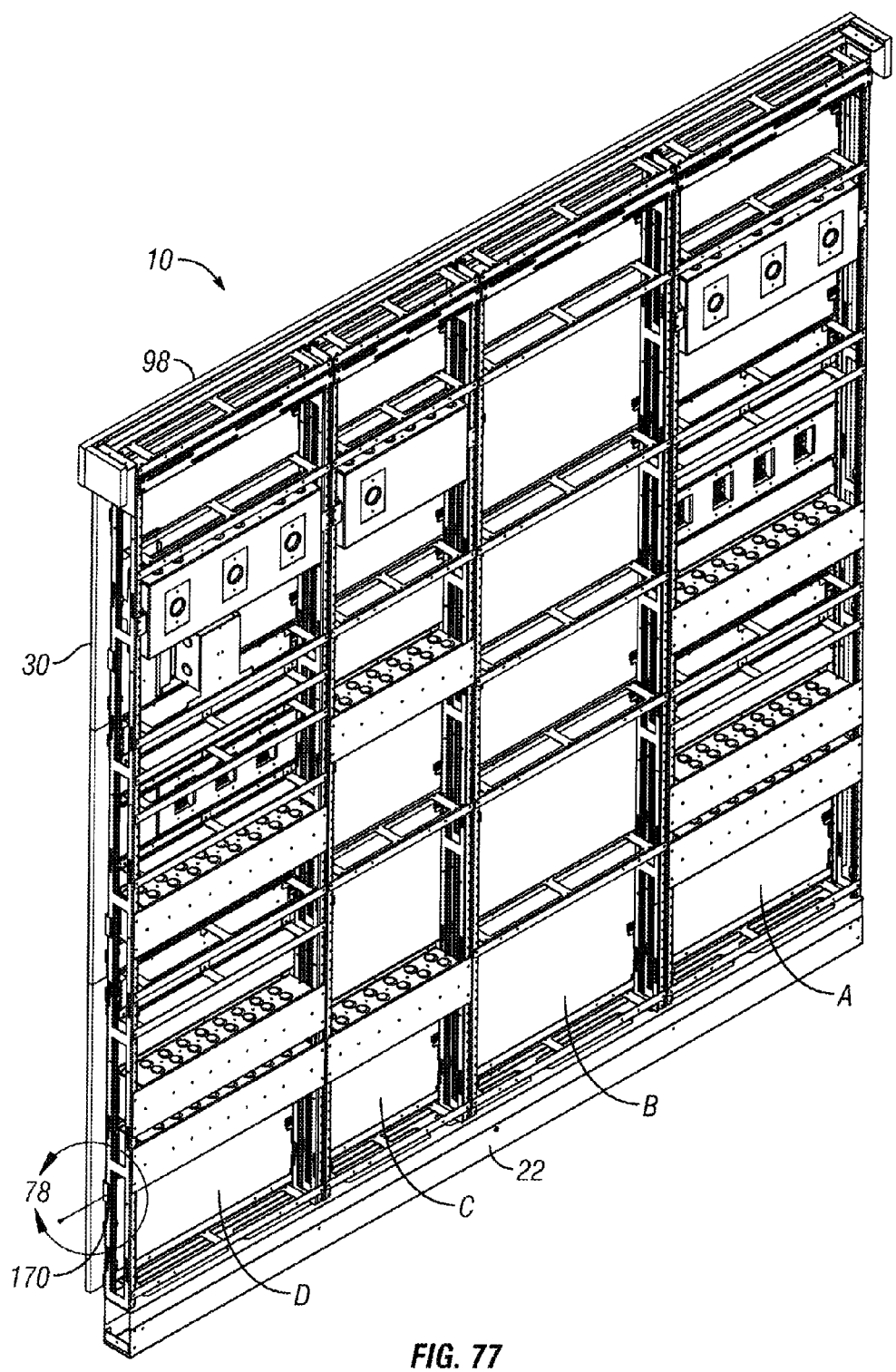
FIG. 77 is a rear perspective view of the partially assembled headwall showing all four sections with the crown molding assembly in place.
Figure 82:
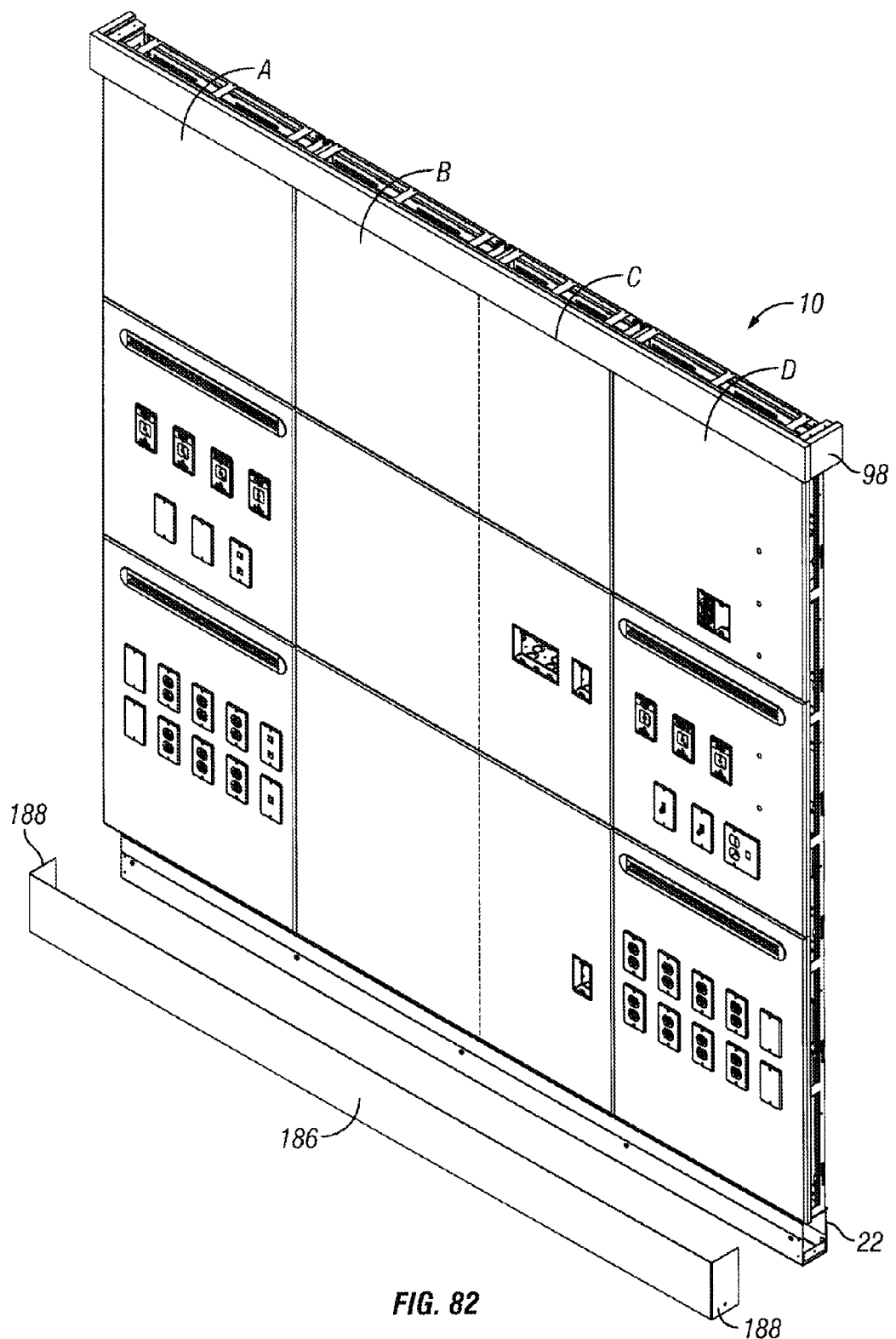
FIG. 82 shows a frontal perspective partially exploded view of the partially assembled headwall with all the cover panels and crown molding in place and illustrating the placement of the trim assembly that encloses the base assembly.

Although the structure of the crown molding trim panel 100 may vary, in this embodiment it is comprised of a front or header panel member 130 and a side or end panel member 132. The header panel 130, shown in FIGS. 60-63 is an elongate member that extends the width of the entire headwall 10. The header panel 130 may include an angled header support bracket 134 for additional support. A suitable support bracket 134 is shown in FIGS. 57-59.

The left end 136 of the header panel 130 is attached to the front flange 124 of the crown molding support bracket 116 as by a screw 138. The end panel 132 is attached to the side flange 126 of the crown molding support bracket 116 with screws 140. Thus, the crown molding support bracket 116 serves to unite the end and header panels 132 and 130 as well as attach these members to the adjustment bracket 102L. As is also seen in FIG. 47, the header support bracket 134 may be attached to the back of the header panel 130 by screws 140.

The assembled trim assembly 98 is positioned on the top of the head system with the crown molding support bracket 116 aligned with the attachment flange 108 and then secured with screws. Then, with the screws 110a and 110b (FIG. 48) in the slotted flange 106 of the adjustment bracket 102L loosened, the crown molding trim panel 100 can be adjusted to meet the ceiling line 18. Thus, the adjustable connection between the crown molding trim panel 100 and the header system, the upper edge 150 of the crown molding can be made flush with the ceiling even if the ceiling line is not level. In most instances, the width of the crown molding trim panel 100 will be about the same as the width of the adjoined headwall sections, and the vertical dimension of the trim panel will be sized to extend from the top of the headwall to the ceiling and thereby to conceal the gap between the top of the headwall and the ceiling line.

When the attachment and adjustment of the upper trim assembly 98 is complete, the cover panels 30 may be attached to complete the matrix of panels on the front of the headwall system 10. In accordance with the preferred embodiment of the invention, the headwall system 10 includes a panel hanger assembly for each panel that is to be attached. A preferred panel hanger assembly is illustrated in FIGS. 67-76, to which attention now is directed.

The panel hanger assembly comprises one or more up-hooks 160 on the front of the chassis CH. The up-hooks are conveniently attached to the front of the studs, as shown in FIG. 48. However, the number, shape and position of the up-hooks 160 may vary. The panel hanger assembly further comprises one or more down-hooks 162, which are sized and positioned to mate with the up-hooks 160, as illustrated in FIG. 67-70. As shown, each panel first is placed up against the studs. The upper edge of the uppermost panels 30 should be tucked up under the upper trim assembly 98 (FIGS. 67 & 68) behind the crown molding trim panel 100 and then pivoted into place against the stud and then slid downward until the down-hooks 162 engage the up hooks 160 as shown.

Now it will be understood that the while the engaged up-hooks 160 and down-hooks 162 securely attach the panels to the frames C of the header sections A, B, C, and D, the shape of the hooks also allows slight movement of the panels laterally (side to side) and vertically without permitting movement of the panel forward or rearward. This ensures that all the panels in the completed matrix will be properly aligned relative to the others. In this way, when all the panels 30 have been attached, they may be adjusted so that all the seams are tight and aligned properly. Once this final alignment is completed, the panels may be stabilized or locked into position using locking brackets, as shown in FIG. 77-81.

A locking bracket 170 may be attached to the exposed side edge of each panel 30 on the end headwall sections A and D. The bracket 170 may be a simple L-shaped member having one side 172 attached to the back of the panel 30 and side 174 attachable to the side of the stud $RS_D$, as shown best in FIG. 78, using a screw 180. The sides 172 and 174 may include elongate slots 176 (FIG. 81) and 178 (FIG. 79), respectively, to allow for slight repositioning of the panels 30.

When the matrix of panels 30 is aligned and locked into place, the finishing trim assemblies may be attached. A base trim cover 186 is shown in FIGS. 82-85. The base trim cover 186 may be a simple elongate panel of an attractive and preferably slightly flexible material with rearwardly turned ends 188. It may be installed by tucking the top edge up under the bottom edge of the bottom panels 30, pivoting the cover 186 into place, and then attaching the cover with screws (not shown).

Figure 86:
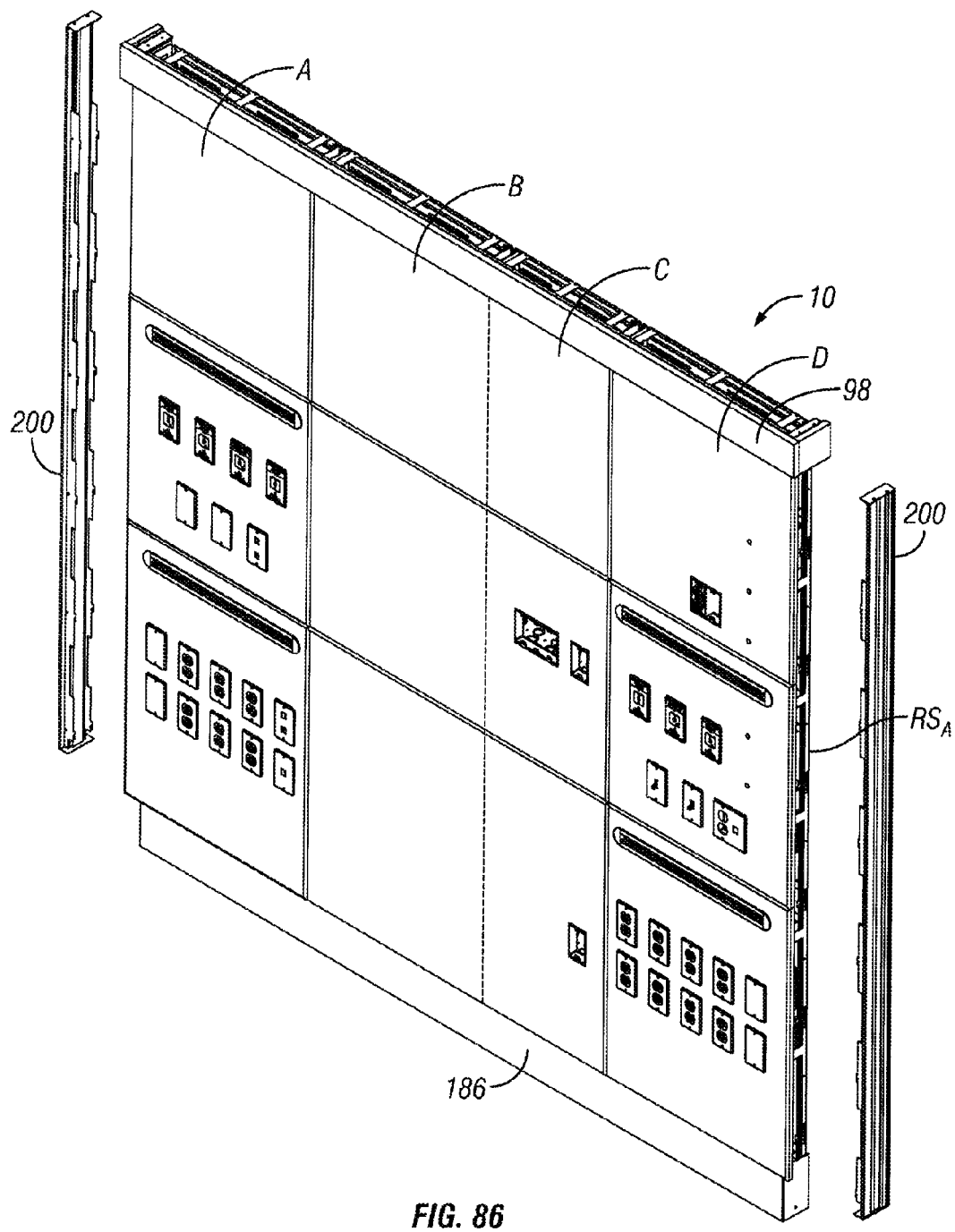
FIG. 86 is a front elevational view of the head assembly with the crown molding and base trim assemblies in place and showing the placement of the side trim assemblies.

As shown in FIG. 86, the headwall system 10 also preferably includes side trim assemblies, both designated as 200. As will be explained in more detail hereafter, the side trim assemblies 200 attach to the exposed studs, names the left stud of the headwall section A, $LS_A$ (not seen in FIG. 86), and the right stud of the headwall section D, $RS_D$. They attach using the same hook and slot system as used to interlock the headwall sections as previously described. Now it will be understood why the left stud of the headwall section A is oriented with the slots 90 exposed and the hooks 88 extending inwardly as described above in reference to FIG. 45.

Figure 87:
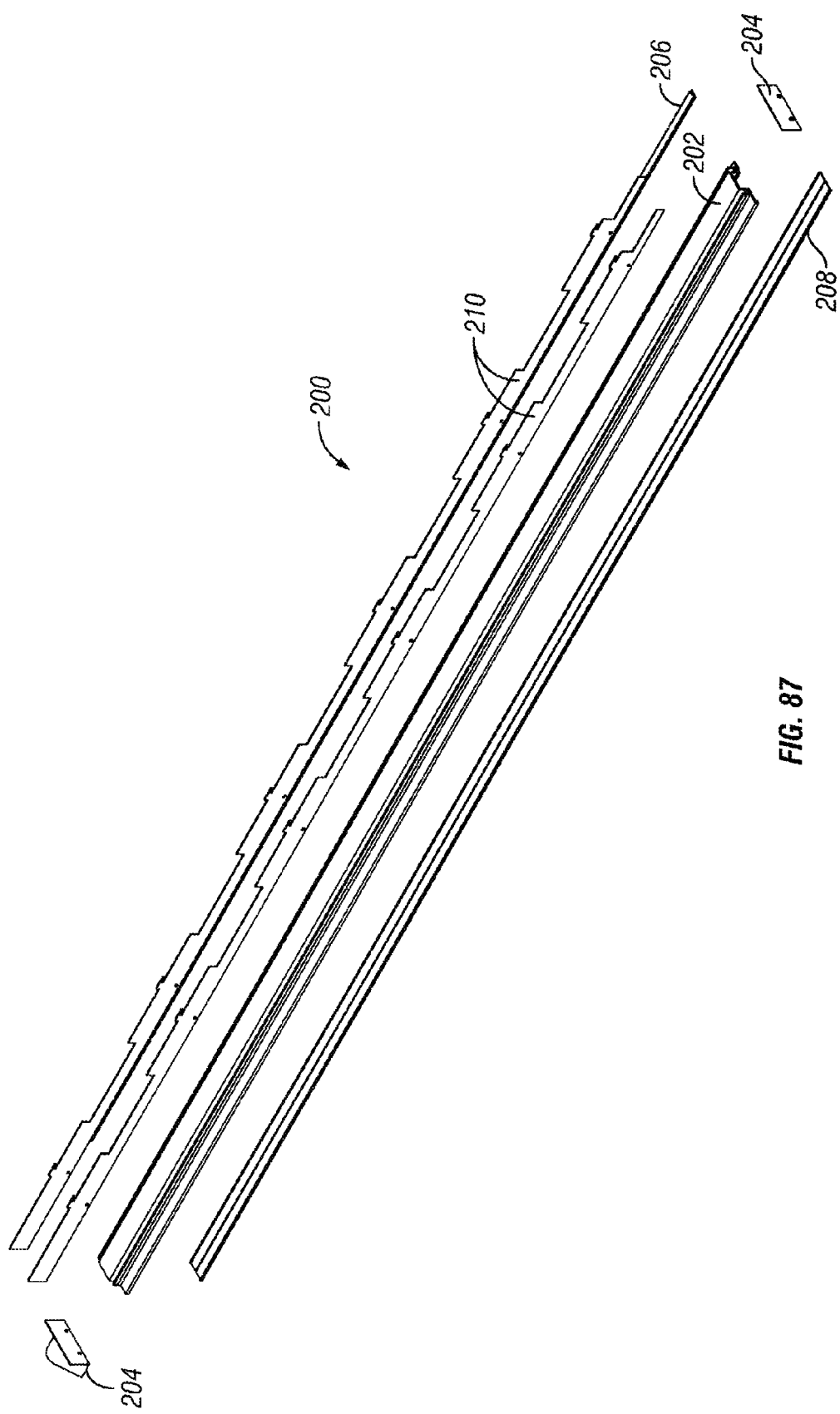
FIG. 87 is an exploded perspective view of the side trim assembly.
Figure 88:
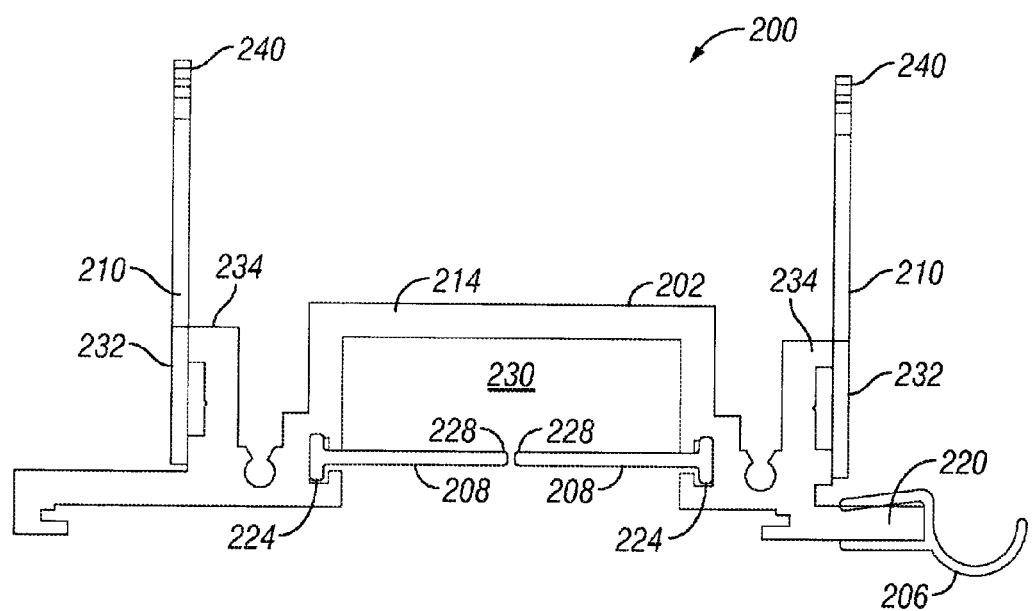
FIG. 88 is an end elevational view of the assembled side trim assembly.
Figure 89:
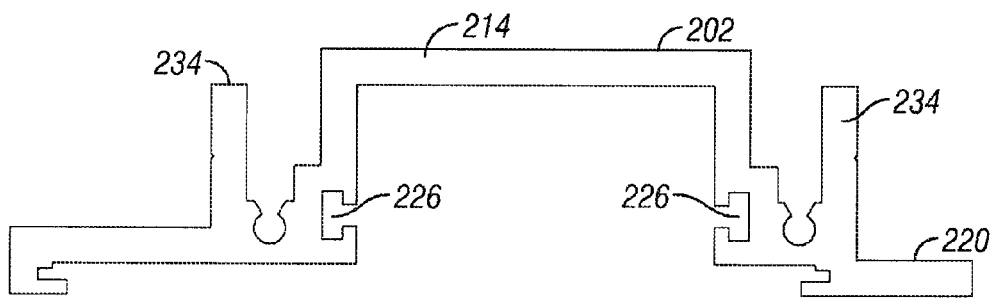
FIG. 89 is an end elevational view of the side trim member of the side trim assembly.
Figure 90:
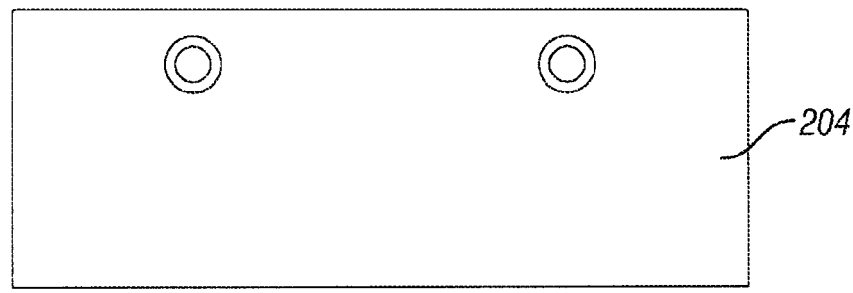
FIG. 90 is a side elevational view of the end plate for the side trim assembly.

A seen in FIGS. 87-89, the side trim assembly 200 generally comprises a vertical trim member 202, a pair of end plates 204 (FIG. 87), a drywall trim flap 206, a pair of cord management flaps 208, and a pair of mounting brackets 210. The vertical trim member 202 is an elongate member formed with a profile to receive the other components and consolidate them into a unitary whole. The main body 214 of the trim member 202 with the end plates 204 (FIG. 90) encloses the sides of the headwall system providing a finished appearance.

Figure 91:
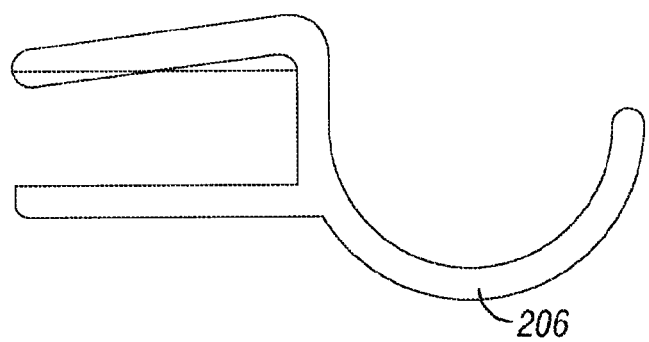
FIG. 91 is an end elevational view of the flexible wall trim strip of the side trim assembly.
Figure 92:
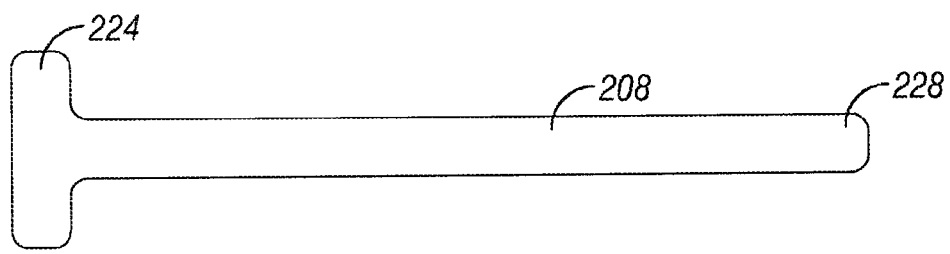
FIG. 92 is an end elevational view of one of the flap members that form the cable management trim.

The flexible drywall trim flap 206 (FIG. 91) clips onto a wall side flange 220 (FIGS. 88 & 89) on the trim member 202. Each of the cord management flaps 206 has a spine 224 that is received in a groove 226 (FIG. 89) on the inside profile of the trim member 202. The flaps 206 are sized so that the terminal edges 228 are immediately adjacent but allow easy access to cord receiving channel 230 (FIG. 88) formed thereby.

Figure 93:
FIG. 93 is a front elevational view of one of the mounting brackets of the side trim assembly.
Figure 94:
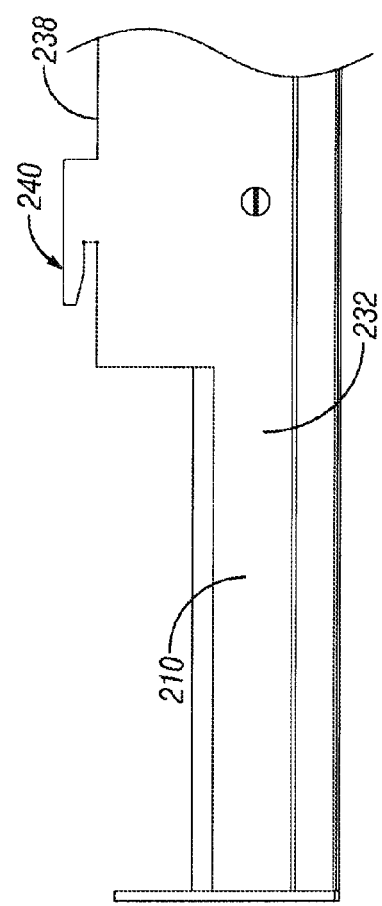
FIG. 94 is an enlarged fragmented view of a portion of the mounting bracket shown in FIG. 93 and illustrating the down hook on the bracket.

The mounting brackets 210 are shown in FIGS. 93 and 94. Each bracket 210 includes a body section 232 (FIG. 94 only) that is sized to be attached to the bracket attachment flanges 234 on the trim member 202 (FIG. 88) by screws (not shown). Extending from the leading edge 238 of the bracket 210 are hooks 240 similar to the hooks 88 on the studs. Thus, the assembled side trim assemblies are mountable on the exposed studs in the same way that one headwall section is attached to the adjacent section. The tops of the side trim assemblies 200 tuck in behind the upper trim assembly 98 like the upper panels 30. After the drywall trim flaps 206 are shaped to the wall surface, caulking may be applied, if desired.

Figure 95:
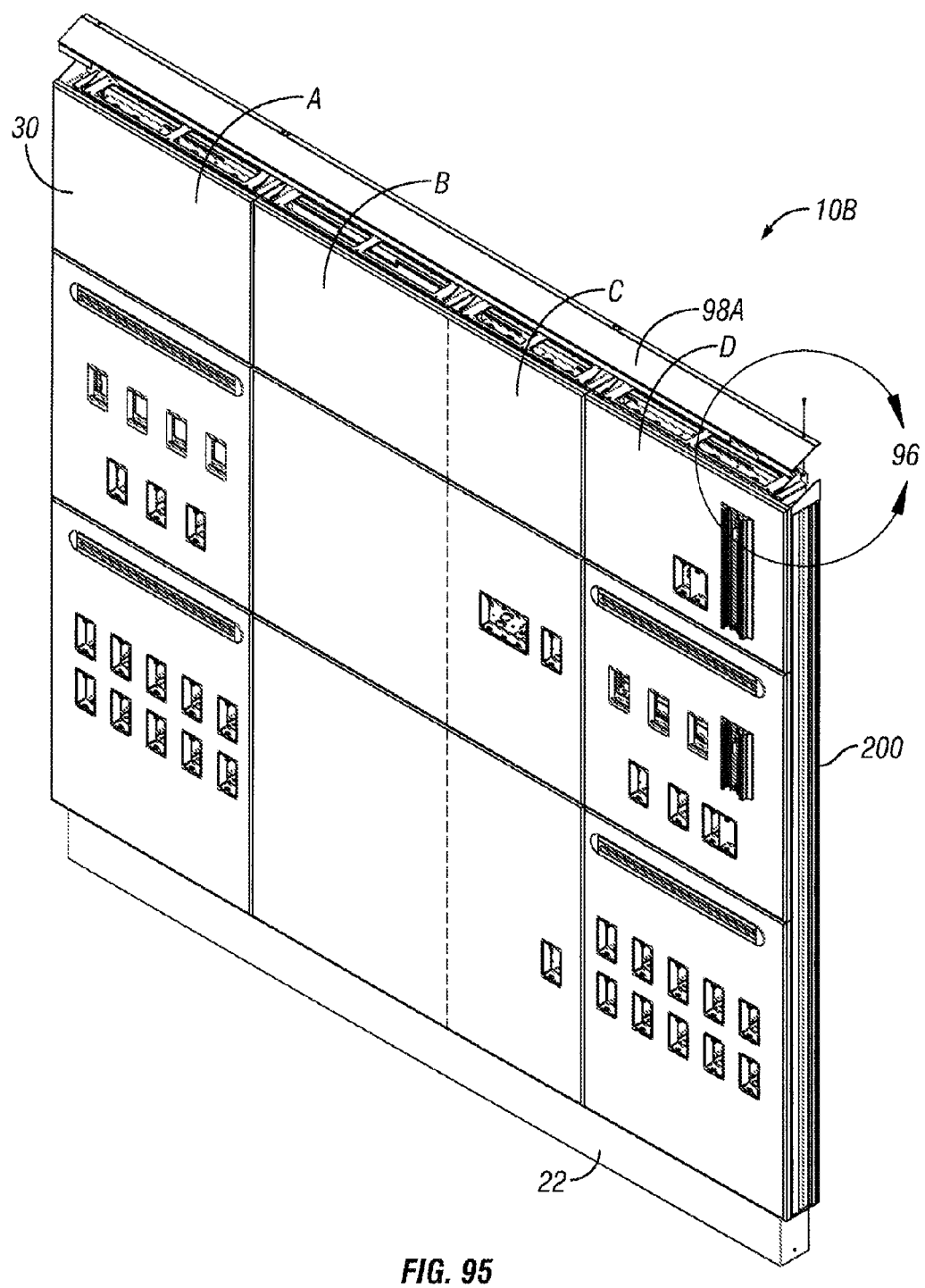
FIG. 95 is a frontal perspective view of a nearly completely assembled headwall assembly where the installed headwall will not reach to the ceiling and showing the installation of a header trim instead of a crown molding trim assembly.
Figure 96:
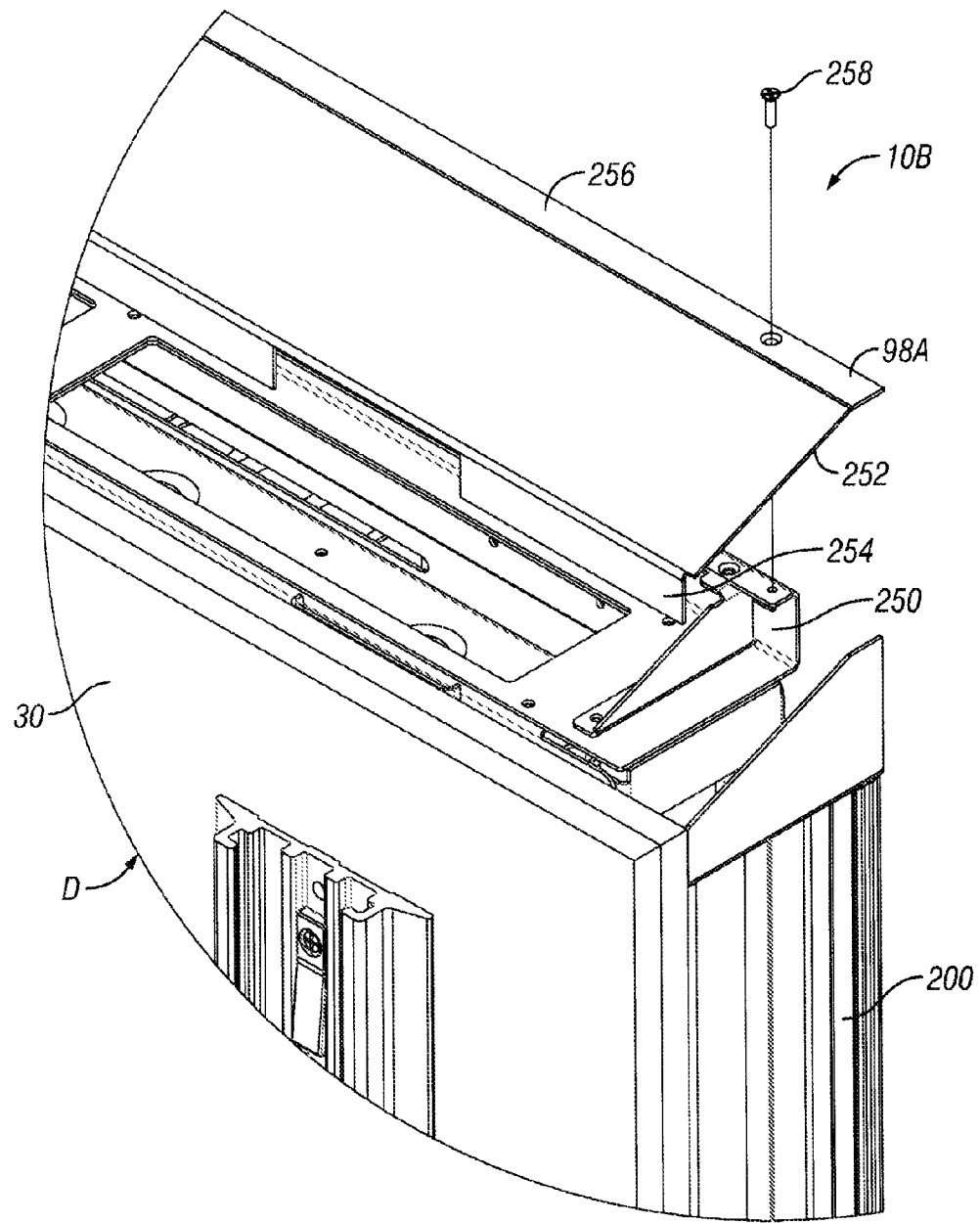
FIG. 96 is an enlarged view of the portion included in the circle identified as 96 in FIG. 95.

Although the above-described embodiment is a headwall that engages the ceiling 18, there may be some instances where the top of the headwall system is a distance below the ceiling. In these cases, a modified upper trim assembly 98A may be provided, as shown in FIGS. 95 and 96. This trim assembly 98A comprises one or more attachment brackets 250 mounted to the top of the frames C and a trim panel 252 with a downwardly extending forward flange 254 that can be fitted behind the upper edge of the top panels. The trim panel includes a rear flange 256 configured to be attached to the mounting bracket 250 by one or more screws 258.

Figure 97:
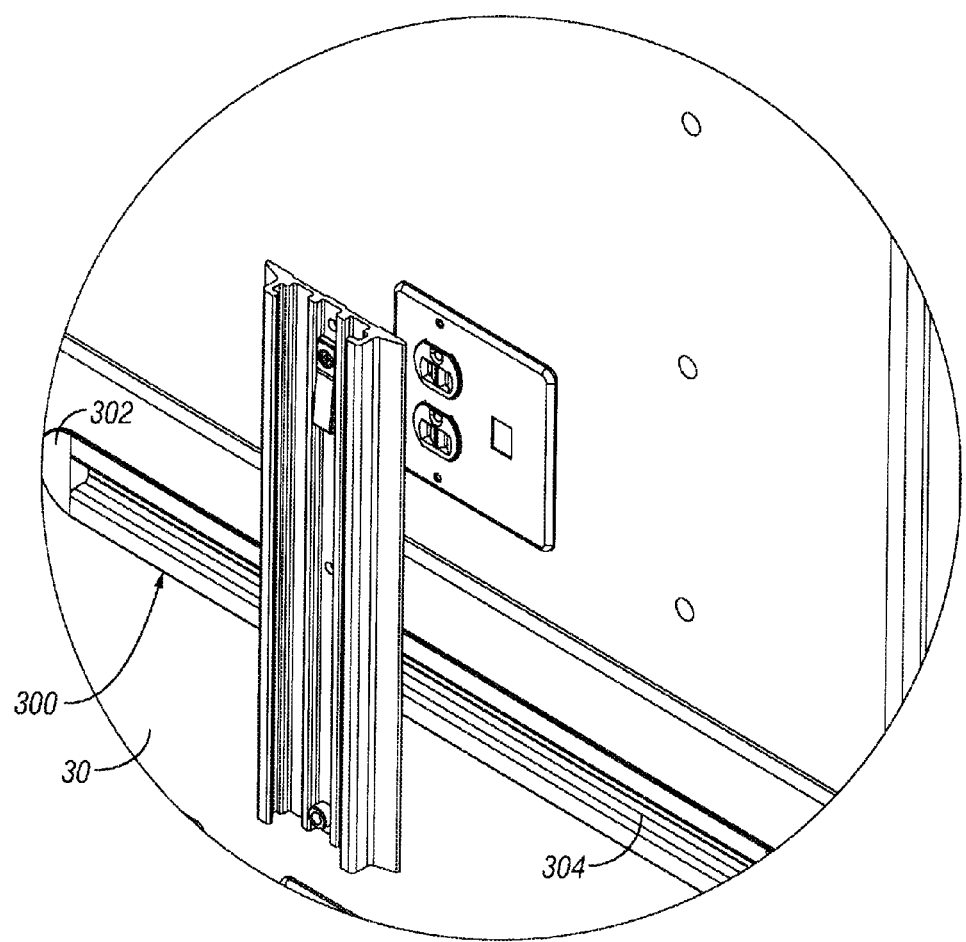
FIG. 97 is an enlarged perspective view of the front of one of the panels showing the recessed equipment track.
Figure 98:
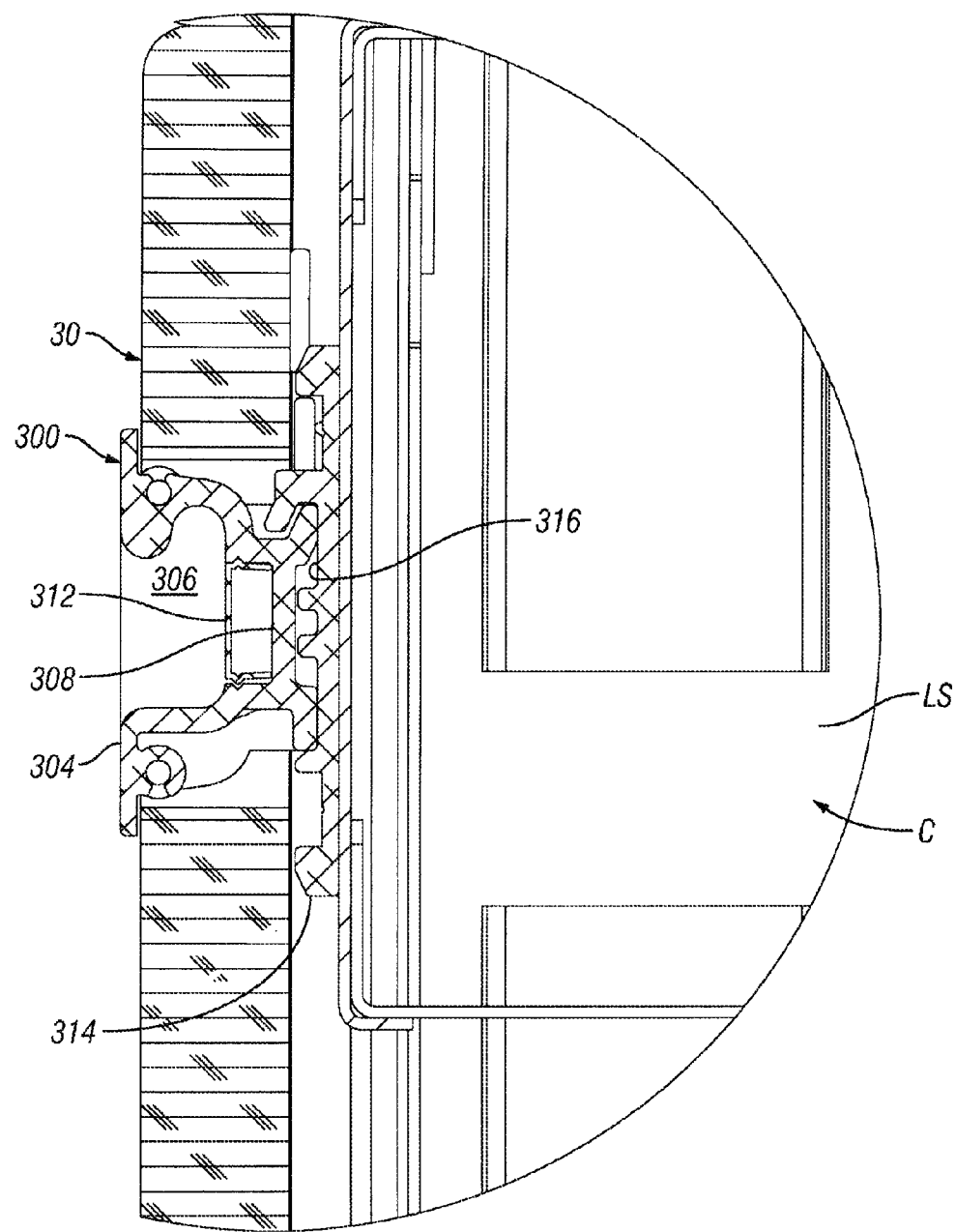
FIG. 98 is an enlarged vertical sectional view through a portion of the front of one of the headwall sections showing the profile of the recessed equipment track.

Yet another advantageous feature of the headwall system 10 of this invention is the strategically place equipment tracks, designated collectively at 300 in FIGS. 1, 97, and 98. As best seen in the enlarged views of FIGS. 97 and 98, these equipment tracks 300 are recessed into the panels 30 so that the opening to the recess is substantially flush with the front surface of the panel. Additionally, the recess is formed in the panel with blind ends 302 (FIG. 97) that terminate a distance from the edge or periphery of the panel. This reduces the crevices available to harbor harmful microorganisms and enables intended use of sanitizers to facilitate effective infection control measures.

As best seen in FIG. 98, the track is an elongate member 304 with a profile that defines a main recess 306 selected to mate with commercially available equipment brackets. A groove 308 is provided along the rear wall of the track member 304 to allow for screws or other fasteners (not shown) that attach the member to the structural support behind it. A vinyl snap-in screw cover strip 312 may be inserted in the groove to cover the screw heads. For added structural support and ease of assembly, a ribbed support bar 314 may be attached to the chassis CH behind the track 300. The support bar 314 includes a recess 316 to receiving the rear profile of the elongate track member 304. This holds the member 304 in place until the fasteners are applied. Now it will appreciated that this construction allows the track to be embedded in the panel 30 rather than fixed on the surface of it.

Now it will be appreciated that the modular medical headwall system of the present invention provides several advantages at both the manufacturing level as well as at the point of installation. The configuration of the headwall sections allows the number and configuration of the sections in a particular headwall to be selected according to the customer's specifications. The studs in each frame section include hooks and slots that ensure secure attachment of one section to each adjacent section while maintaining proper alignment. For floor-mounted applications, a self-leveling base assembly provides a level support track even on uneven floors. An adjustable crown molding assembly provides an attractive architectural feature while concealing an irregular ceiling line. The cover panels forming the front of the headwall float on a hanger system that allows slight horizontal and vertical movement while holding the entire matrix of panels firmly against the frame behind it; this allows the panels to maintain proper alignment in the assembled headwall even where the supporting wall and floor surfaces are irregular. The side trim assembly includes a cable management recess. Some panels include a floating equipment track that is aesthetically pleasing and less likely to harbor microorganisms.

The embodiments shown and described above are exemplary. Many details are often found in the art and, therefore, many such details are neither shown nor described herein. It is not claimed that all of the details, parts, elements, or steps described and shown were invented herein. Even though numerous characteristics and advantages of the present inventions have been described in the drawings and accompanying text, the description is illustrative only. Changes may be made in the details, especially in matters of shape, size, and arrangement of the parts within the principles of the inventions to the full extent indicated by the broad meaning of the terms of the attached claims. The description and drawings of the specific embodiments herein do not point out what an infringement of this patent would be, but rather provide an example of how to use and make the invention. Likewise, the abstract is neither intended to define the invention, which is measured by the claims, nor is it intended to be limiting as to the scope of the invention in any way. Rather, the limits of the invention and the bounds of the patent protection are measured by and defined in the following claims.

What is claimed is:

1. A modular medical headwall system for mounting on a wall of a structure having a floor and a ceiling, the system comprising:
   a plurality of headwall sections including a first section and a second section, wherein each of the headwall sections is configured to be arranged side by side with another headwall section to form a headwall, and wherein each such headwall section comprises:
      a frame comprising first and second studs and having a width and a bottom; and
      at least one medical service outlet supported on the frame; and a base assembly comprising:
  a horizontal support track configured to receive the bottom of the plurality of headwall sections when the head wall sections are arranged side by side; and
  a floor rail attachable to the floor of the structure;
  wherein the support track is adjustably supportable on the floor rail so that when the head wall sections are arranged side by side in the support track the plurality of headwall sections can be collectively leveled regardless of irregularities in the floor.

2. The modular medical headwall system of claim 1 wherein when the first and second headwall sections are arranged side by side the second stud of the first headwall section abuts the first stud of the second headwall section, wherein one of the second stud of the first headwall section and the first stud of the second headwall section includes a hook and the other of the second stud of the first headwall section and the first stud of the second headwall section includes a slot sized to receive the hook, whereby the engagement of the hook in the slot attaches the first headwall section to the second headwall section and ensures that the first and second headwall sections are aligned vertically and horizontally.

3. The modular medical headwall system of claim 2 wherein the head wall formed by the plurality of head wall sections arranged side by side has an assembled width and a top, and wherein the system further comprises:
  a crown molding trim panel having an upper edge, a width about the same as the assembled width of the headwall, and a vertical dimension sized to extend from the top of the headwall to the ceiling, and wherein the crown molding trim panel is adjustably connectable to the top of the headwall so that the trim panel can be positioned to abut the ceiling when the top of the headwall is level and the ceiling line is unlevel.

4. The modular medical headwall system of claim 3 wherein the frame of each headwall section has a front and includes an up hook on the front, wherein each headwall section further comprises a panel having a rear surface and a down hook on the rear surface, the panel being supportable on the front of the frame by having the down hook hang on the up hook, and wherein the down hook on the panel and the up hook on the frame are configured to permit lateral and vertical alignment of the panel without permitting movement of the panel forward or rearward.

5. The modular medical headwall system of claim 4 wherein each of the panels has a front surface and a periphery and wherein the system further comprises:
  an equipment track in at least one of the panels on at least one of the plurality of headwall sections, the equipment track comprising an elongate recess with first and second blind ends, wherein the track is formed in the panel so that the opening of the track is substantially flush with the front surface of the panel and so that the blind ends of the track are a distance from the periphery.

6. The modular medical headwall system of claim 1 wherein the head wall formed by the plurality of head wall sections arranged side by side has a width and a top, and wherein the system further comprises:
  a crown molding trim panel having an upper edge, a width about the same as the width of the headwall, and a vertical dimension sized to extend from the top of the headwall to the ceiling, and wherein the crown molding trim panel is adjustably connectable to the top of the headwall so that the trim panel can be positioned to abut the ceiling when the top of the headwall is level and the ceiling line is unlevel.

7. The modular medical headwall system of claim 1 wherein the frame of each headwall section has a front and includes an up hook on the front, wherein each headwall section further comprises a panel having a rear surface and a down hook on the rear surface, the panel being supportable on the front of the frame by having the down hook hang on the up hook, and wherein the down hook on the panel and the up hook on the frame are configured to permit lateral and vertical alignment of the panel without permitting movement of the panel forward or rearward.

8. The modular medical headwall system of claim 1 wherein at least one of the plurality of headwall sections further comprises a panel, wherein the panel has a front surface and a periphery, and wherein the system further comprises:
  an equipment track on at least one of the plurality of headwall sections, the equipment track comprising an elongate recess with first and second blind ends, wherein the track is formed in the panel so that the opening of the track is substantially flush with the front surface of the panel and so that the blind ends of the track are a distance from the periphery.

9. The modular medical headwall system of claim 1 wherein the floor rail comprises:
  a U-shaped bottom member; and
  an inverted U-shaped top member received in the bottom member.

10. The modular medical headwall system of claim 9 wherein the bottom member and the top member of the floor rail are both slotted.

11. The modular medical headwall system of claim 10 wherein the support track is slotted.

12. The modular medical headwall system of claim 10 wherein the support track is pivotally attached to the floor rail.

13. The modular medical headwall system of claim 1 wherein the support track is pivotally attached to the floor rail.

14. The modular medical headwall system of claim 1 wherein the support track is L-shaped.

15. The modular medical headwall system of claim 1 wherein the base assembly has a width, wherein the headwall formed by the plurality of headwall sections has an assembled width about the same as the width of the base assembly.

16. A modular medical headwall system for mounting on a wall of a structure having a floor and a ceiling, the system comprising:
  a plurality of headwall sections including a first section and a second section, wherein each of the headwall sections is configured to be arranged side by side with another headwall section to form a headwall, and wherein each such headwall section comprises:
    a frame comprising right and left studs; and
    a plurality of medical service outlets supported on the frame;
  wherein when the first and second headwall sections are arranged side by side, the right stud of the first headwall section abuts the left stud of the second headwall section; and
  wherein one of the right stud of the first headwall section and the left stud of the second headwall section includes a hook and the other of the right stud of the first headwall section and the left stud of the second headwall section includes a slot sized to receive the hook whereby the engagement of the hook in the slot attaches the first headwall section to the second headwall section and ensures that the first and second headwall sections are aligned vertically and horizontally.

17. A modular medical headwall system for mounting on a wall of a structure having a floor and a ceiling, the system comprising:
- a plurality of headwall sections including a first section and a second section, wherein each of the headwall sections is configured to be arranged side by side with another headwall section to form a headwall with an assembled width and a top, and wherein each such headwall section comprises:
  - a frame; and
  - at least one medical service outlet supported on the frame; and
- a crown molding trim panel having an upper edge, a width about the same as the assembled width of the headwall, and a vertical dimension sized to extend from the top of the headwall to the ceiling, and wherein the crown molding trim panel is adjustably connectable to the top of the headwall so that the trim panel can be positioned to abut the ceiling when the top of the headwall is level and the ceiling line is unlevel.

* * * * *

UNITED STATES PATENT AND TRADEMARK OFFICE
CERTIFICATE OF CORRECTION

Page 1 of 1

PATENT NO. : 9,010,031 B1
APPLICATION NO. : 14/015672
DATED : April 21, 2015
INVENTOR(S) : Travis W. Webb, Taylor C. Culpepper and John R. Pierson It is certified that error appears in the above-identified patent and that said Letters Patent is hereby corrected as shown below:

In the Specification:

Column 2, line 41: replace "46 a" with --46 is a--.
Column 3, line 9: replace "63 an" with --63 is an--.
Column 3, line 29: replace "is front" with --is a front--.
Column 3, line 57: replace "is fragmented" with --is a fragmented--.
Column 7, line 27: replace "about" with --abut--.
Column 8, line 39: replace "that the while" with --that while--.
Column 9, line 12: replace "A" with --As--.
Column 9, line 52: replace "place" with --placed--.
Column 10, line 6: replace "to" with --for--.
Column 10, line 8: replace "will appreciated" with --will be appreciated--.

In the Claims:

Column 11, line 13: replace "side the" with --side, the--.

Signed and Sealed this
Twenty-fifth Day of August, 2015

Michelle K. Lee
*Director of the United States Patent and Trademark Office*